US012708594B2

(12) United States Patent
Cochran et al.

(10) Patent No.: US 12,708,594 B2
(45) Date of Patent: Aug. 18, 2026

(54) SULFATE FREE PERSONAL CLEANSING COMPOSITION COMPRISING LOW INORGANIC SALT

(71) Applicant: The Procter & Gamble Company, Cincinnati, OH (US)

(72) Inventors: Brooke Michele Cochran, Cincinnati, OH (US); Brian Xiaoqing Song, Mason, OH (US); Howard David Hutton, III, Oregonia, OH (US); Andrei Sergeevich Bureiko, Cincinnati, OH (US); Peter Herbert Koenig, Montgomery, OH (US)

(73) Assignee: THE PROCTER & GAMBLE COMPANY, Cincinnati, OH (US)

(*) Notice: Subject to any disclaimer, the term of this patent is extended or adjusted under 35 U.S.C. 154(b) by 310 days.

(21) Appl. No.: 18/637,740

(22) Filed: Apr. 17, 2024

(65) Prior Publication Data

US 2024/0277584 A1 Aug. 22, 2024

Related U.S. Application Data

(63) Continuation of application No. 18/083,741, filed on Dec. 19, 2022, now Pat. No. 11,992,540, which is a continuation of application No. 16/156,066, filed on Oct. 10, 2018, now abandoned.

(60) Provisional application No. 62/570,377, filed on Oct. 10, 2017.

(51) Int. Cl.

| | |
|---|---|
| ***A61K 8/04*** | (2006.01) |
| ***A61G 5/12*** | (2006.01) |
| ***A61K 8/20*** | (2006.01) |
| ***A61K 8/44*** | (2006.01) |
| ***A61K 8/46*** | (2006.01) |
| ***A61K 8/73*** | (2006.01) |
| ***A61K 8/81*** | (2006.01) |
| ***A61K 8/89*** | (2006.01) |
| ***A61Q 5/00*** | (2006.01) |
| ***A61Q 5/02*** | (2006.01) |
| ***A61Q 5/12*** | (2006.01) |
| ***A61Q 19/10*** | (2006.01) |

(52) U.S. Cl.

CPC ................ *A61K 8/046* (2013.01); *A61G 5/12* (2013.01); *A61K 8/20* (2013.01); *A61K 8/44* (2013.01); *A61K 8/442* (2013.01); *A61K 8/466* (2013.01); *A61K 8/731* (2013.01); *A61K 8/737* (2013.01); *A61K 8/817* (2013.01); *A61K 8/89* (2013.01); *A61Q 5/006* (2013.01); *A61Q 5/02* (2013.01); *A61Q 19/10* (2013.01); *A61K 2800/262* (2013.01); *A61K 2800/30* (2013.01); *A61K 2800/5426* (2013.01); *A61K 2800/596* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 1,489,388 | A | 4/1924 | Glenn |
| 1,600,340 | A | 9/1926 | Hoffman |
| 1,612,255 | A | 12/1926 | William |
| 2,438,091 | A | 3/1948 | Lynch |
| 2,528,378 | A | 10/1950 | Mannheimer |
| 2,658,072 | A | 11/1953 | Milton |
| 2,809,971 | A | 10/1957 | Jack et al. |
| 2,879,231 | A | 3/1959 | Marshall |
| 3,219,656 | A | 11/1965 | Boettner |
| 3,236,733 | A | 2/1966 | Karsten et al. |
| 3,373,208 | A | 3/1968 | Blumenthal |
| 3,636,113 | A | 1/1972 | Hall |
| 3,709,437 | A | 1/1973 | Wright |
| 3,716,498 | A | 2/1973 | Hall |
| 3,753,196 | A | 8/1973 | Kurtz et al. |
| 3,761,418 | A | 9/1973 | Parran |
| 3,792,068 | A | 2/1974 | Luedders et al. |
| 3,887,692 | A | 6/1975 | Gilman |
| 3,904,741 | A | 9/1975 | Jones et al. |
| 3,950,532 | A | 4/1976 | Bouillon et al. |
| 3,959,160 | A | 5/1976 | Horsler et al. |
| 4,049,792 | A | 9/1977 | Elsnau |
| 4,089,945 | A | 5/1978 | Brinkman et al. |
| 4,120,948 | A | 10/1978 | Shelton |
| 4,137,180 | A | 1/1979 | Naik |
| 4,237,155 | A | 12/1980 | Kardouche |
| 4,309,119 | A | 1/1982 | Wittersheim |

(Continued)

FOREIGN PATENT DOCUMENTS

| | | | |
|---|---|---|---|
| BE | 825146 | A | 8/1975 |
| BR | 199400875 | A | 10/1995 |

(Continued)

OTHER PUBLICATIONS

"Anti-Dandruff Shampoo", Mintel Database, Record No. 752198, dated Aug. 2007 ; pp. 1-3.

"Comparative Study on the Chemical constituents of Aloe Vera and Aloe Kula in China", Zhang Xiaohua et al., Flavor Cosmetics, No. 63, dated Dec. 31, 2000, pp. 7-11.

"Dandruff Control Shampoo" , Mintel Database, Record No. 2300131, dated Jan. 2014; pp. 1-2.

(Continued)

*Primary Examiner* — Brian Gulledge

(74) *Attorney, Agent, or Firm* — Matthew J. Spegele; Angela K. Haughey

(57) ABSTRACT

Sulfate-free personal cleansing compositions that include an acyl taurate anionic surfactant, a cationic deposition polymer, little or no inorganic salt and an aqueous carrier. The composition is phase stable, avoids in situ coacervate formulation and forms a coacervate upon dilution with water.

13 Claims, No Drawings

(56) References Cited

U.S. PATENT DOCUMENTS 4,323,683 A 4/1982 Bolich, Jr. et al.
4,329,334 A 5/1982 Su et al.
4,345,080 A 8/1982 Bolich, Jr.
4,359,456 A 11/1982 Gosling et al.
4,379,753 A 4/1983 Bolich, Jr.
4,430,243 A 2/1984 Bragg
4,470,982 A 9/1984 Winkler
4,726,945 A 2/1988 Patel
4,732,696 A 3/1988 Urfer
4,839,166 A 6/1989 Grollier et al.
4,854,333 A 8/1989 Inman et al.
4,867,971 A 9/1989 Ryan et al.
4,931,274 A 6/1990 Barabino et al.
4,973,416 A 11/1990 Kennedy
4,985,238 A 1/1991 Tanner et al.
4,997,641 A 3/1991 Hartnett
5,019,375 A 5/1991 Tanner et al.
5,093,112 A 3/1992 Birtwistle et al.
5,104,646 A 4/1992 Bolich, Jr.
5,106,609 A 4/1992 Bolich, Jr.
5,135,747 A 8/1992 Faryniarz et al.
5,156,834 A 10/1992 Beckmeyer et al.
5,294,644 A 3/1994 Login et al.
5,296,157 A 3/1994 Macgilp et al.
5,296,622 A 3/1994 Uphues
5,298,640 A 3/1994 Callaghan et al.
5,332,569 A 7/1994 Wood et al.
5,364,031 A 11/1994 Taniguchi et al.
5,374,421 A 12/1994 Tashiro
5,374,614 A 12/1994 Behan et al.
5,409,695 A 4/1995 Abrutyn et al.
5,415,810 A 5/1995 Lee et al.
5,417,965 A 5/1995 Janchitraponvej et al.
5,429,816 A 7/1995 Hofrichter et al.
5,439,682 A 8/1995 Wivell
5,441,659 A 8/1995 Minor
5,486,303 A 1/1996 Capeci
5,489,392 A 2/1996 Capeci
5,496,488 A 3/1996 Kacher et al.
5,516,448 A 5/1996 Capeci
5,536,493 A 7/1996 Dubief
5,554,588 A 9/1996 Behan et al.
5,560,918 A 10/1996 Wivell
5,565,422 A 10/1996 Del
5,569,645 A 10/1996 Dinniwell
5,574,005 A 11/1996 Welch
5,576,282 A 11/1996 Miracle
5,578,298 A 11/1996 Berthiaume
5,595,967 A 1/1997 Miracle
5,597,936 A 1/1997 Perkins
5,599,549 A 2/1997 Wivell
5,614,180 A 3/1997 Chung
5,624,666 A 4/1997 Coffindaffer et al.
5,635,469 A 6/1997 Fowler et al.
5,665,267 A 9/1997 Dowell et al.
5,691,297 A 11/1997 Nassano
5,714,137 A 2/1998 Trinh
5,747,436 A 5/1998 Patel
5,776,444 A 7/1998 Birtwistle et al.
5,800,897 A 9/1998 Sharma
5,816,446 A 10/1998 Steindorf et al.
5,830,440 A 11/1998 Sturla et al.
5,853,618 A 12/1998 Barker
5,879,584 A 3/1999 Bianchetti
5,891,424 A 4/1999 Bretzler et al.
5,902,225 A 5/1999 Monson
5,925,603 A 7/1999 D'Angelo
5,942,217 A 8/1999 Woo et al.
5,976,514 A 11/1999 Guskey et al.
5,980,877 A 11/1999 Baravetto
5,985,939 A 11/1999 Minor
6,015,547 A 1/2000 Yam
6,015,780 A 1/2000 Llosas Bigorra et al.
6,020,303 A 2/2000 Cripe et al.
6,039,933 A 3/2000 Samain et al.
6,046,152 A 4/2000 Vinson et al.
6,060,443 A 5/2000 Cripe et al.
6,087,309 A 7/2000 Vinson et al.
6,110,451 A 8/2000 Matz et al.
6,133,222 A 10/2000 Vinson et al.
6,139,828 A 10/2000 Mccullough
6,153,567 A 11/2000 Hughes
6,153,569 A 11/2000 Halloran
6,162,834 A 12/2000 Sebillotte-Arnaud et al.
6,180,121 B1 1/2001 Guenin et al.
6,225,464 B1 5/2001 Hiler
6,231,844 B1 5/2001 Nambu
6,232,302 B1 5/2001 Alberico et al.
6,248,135 B1 6/2001 Trinh et al.
6,268,431 B1 7/2001 Snyder et al.
6,284,225 B1 9/2001 Bhatt
6,329,331 B1 12/2001 Aronson
6,335,312 B1 1/2002 Coffindaffer et al.
6,352,688 B1 3/2002 Scavone et al.
6,386,392 B1 5/2002 Argentieri
6,413,920 B1 7/2002 Bettiol
6,423,305 B1 7/2002 Cauwet-Martin et al.
6,426,326 B1 7/2002 Mitra et al.
6,436,442 B1 8/2002 Woo et al.
6,451,300 B1 9/2002 Dunlop et al.
6,458,857 B1 10/2002 Wittenbrink et al.
6,488,943 B1 12/2002 Beerse et al.
6,511,669 B1 1/2003 Garnier et al.
6,565,863 B1 5/2003 Guillou et al.
6,579,907 B1 6/2003 Sebillotte-Arnaud et al.
6,627,585 B1 9/2003 Steer
6,642,194 B2 11/2003 Harrison
6,649,155 B1 11/2003 Dunlop et al.
6,656,923 B1 12/2003 Trinh
6,660,288 B1 12/2003 Behan et al.
6,679,324 B2 1/2004 Den et al.
6,716,455 B2 4/2004 Birkel
6,716,805 B1 4/2004 Sherry
6,740,713 B1 5/2004 Busch et al.
6,743,760 B1 6/2004 Hardy et al.
6,764,986 B1 7/2004 Busch et al.
6,767,507 B1 7/2004 Woo et al.
6,794,356 B2 9/2004 Turner
6,814,088 B2 11/2004 Barnabas et al.
6,827,795 B1 12/2004 Kasturi et al.
6,869,923 B1 3/2005 Cunningham
6,897,253 B2 5/2005 Schmucker-Castner
6,908,889 B2 6/2005 Niemiec et al.
6,930,078 B2 8/2005 Wells
6,992,054 B2 1/2006 Unilever
7,018,978 B2 3/2006 Miracle et al.
7,030,068 B2 4/2006 Clare et al.
7,100,767 B2 9/2006 Chomik et al.
7,151,079 B2 12/2006 Fack et al.
7,172,099 B2 2/2007 Hoefte
7,202,198 B2 4/2007 Gordon et al.
7,217,752 B2 5/2007 Schmucker-Castner et al.
7,220,408 B2 5/2007 Decoster et al.
7,223,361 B2 5/2007 Kvietok
7,223,385 B2 5/2007 Gawtrey et al.
7,485,289 B2 2/2009 Gawtrey et al.
7,504,094 B2 3/2009 Decoster et al.
7,531,497 B2 5/2009 Midha et al.
7,541,320 B2 6/2009 Dabkowski et al.
7,598,213 B2 10/2009 Geary et al.
7,659,233 B2 2/2010 Hurley et al.
7,666,825 B2 2/2010 Wagner et al.
7,820,609 B2 10/2010 Soffin et al.
7,829,514 B2 11/2010 Paul et al.
7,841,036 B2 11/2010 Smith
7,867,505 B2 1/2011 Elliott et al.
7,928,053 B2 4/2011 Hecht et al.
7,977,288 B2 7/2011 SenGupta
8,007,545 B2 8/2011 Fujii et al.
8,058,500 B2 11/2011 Sojka et al.
8,084,407 B2 12/2011 Soffin et al.
8,088,721 B2 1/2012 Soffin et al.
8,119,168 B2 2/2012 Johnson
8,124,063 B2 2/2012 Harichian et al.

(56) References Cited

U.S. PATENT DOCUMENTS 8,158,571 B2 4/2012 Alonso
8,300,949 B2 10/2012 Xu
8,322,631 B2 12/2012 Richardson et al.
8,343,469 B2 1/2013 Bierganns et al.
8,349,300 B2 1/2013 Wells
8,357,359 B2 1/2013 Woo et al.
8,361,450 B2 1/2013 Johnson et al.
8,388,699 B2 3/2013 Wood
8,401,304 B2 3/2013 Sportvision
8,435,501 B2 5/2013 Peffly et al.
8,437,556 B1 5/2013 Saisan
8,491,877 B2 7/2013 Schwartz et al.
8,539,631 B2 9/2013 Catalfamo et al.
8,574,561 B1 11/2013 Patel et al.
8,580,725 B2 11/2013 Kuhlman et al.
8,609,600 B2 12/2013 Warr et al.
8,628,760 B2 1/2014 Carter et al.
8,629,095 B2 1/2014 Deleersnyder
8,653,014 B2 2/2014 Hilvert
8,675,919 B2 3/2014 Maladen
8,679,316 B2 3/2014 Brunner et al.
8,680,035 B2 3/2014 Kuhlman et al.
8,699,751 B2 4/2014 Maladen
8,709,337 B2 4/2014 Gruenbacher et al.
8,709,385 B2 4/2014 Tamarkin
8,741,275 B2 6/2014 Dente et al.
8,741,363 B2 6/2014 Albrecht et al.
8,771,765 B1 7/2014 Fernandez
8,772,354 B2 7/2014 Williams et al.
8,795,635 B2 8/2014 Tamarkin et al.
8,877,316 B2 11/2014 Hasenoehrl et al.
8,883,698 B2 11/2014 Scheibel et al.
8,931,711 B2 1/2015 Gruenbacher
8,980,239 B2 3/2015 Staudigel et al.
8,987,187 B2 3/2015 Smets et al.
9,006,162 B1 4/2015 Rizk
9,186,642 B2 11/2015 Dihora et al.
9,187,407 B2 11/2015 Koshti et al.
9,265,727 B1 2/2016 Lowenborg
9,272,164 B2 3/2016 Johnson et al.
9,296,550 B2 3/2016 Smith
9,308,398 B2 4/2016 Hutton et al.
9,393,447 B2 7/2016 Zasloff
9,428,616 B2 8/2016 Wagner
9,511,007 B2 12/2016 Frantz et al.
9,512,275 B2 12/2016 Wagner
9,610,239 B2 4/2017 Feng
9,655,821 B2 5/2017 Carter et al.
9,662,291 B2 5/2017 Johnson et al.
9,682,021 B2 6/2017 Tamarkin et al.
9,776,787 B2 10/2017 Nakajima
9,949,901 B2 4/2018 Zhao et al.
9,949,911 B2 4/2018 Cetti
9,968,535 B2 5/2018 Kitko
9,968,537 B2 5/2018 Sharma
9,993,419 B2 6/2018 Glenn, Jr.
9,993,420 B2 6/2018 Glenn, Jr. et al.
10,039,706 B2 8/2018 Meralli et al.
10,039,939 B2 8/2018 Xavier et al.
10,113,140 B2 10/2018 Frankenbach
10,182,976 B2 1/2019 Staudigel
10,238,685 B2 3/2019 Dunn et al.
10,265,261 B2 4/2019 Park et al.
10,311,575 B2 6/2019 Stofel
10,392,625 B2 8/2019 Jin et al.
10,426,713 B2 10/2019 Song
10,441,519 B2 10/2019 Zhao
10,463,596 B1 11/2019 Custer
10,552,557 B2 2/2020 Frankenbach et al.
10,610,473 B2 4/2020 Hertenstein et al.
10,653,590 B2 5/2020 Torres Rivera
10,799,434 B2 10/2020 Torres Rivera
10,842,720 B2 11/2020 Thompson
10,881,597 B2 1/2021 Lane et al.
10,888,505 B2 1/2021 Johnson
10,912,732 B2 2/2021 Gillis
11,116,703 B2 9/2021 Song et al.
11,116,704 B2 9/2021 Song et al.
11,129,775 B2 9/2021 Song et al.
11,253,450 B2 2/2022 Lane
11,334,694 B2 5/2022 Cetti et al.
11,334,695 B2 5/2022 Cetti et al.
11,904,036 B2 2/2024 Song
12,059,488 B2 8/2024 Adamy et al.
2001/0000467 A1 4/2001 Murray
2001/0006088 A1 7/2001 Lyle
2001/0006621 A1 7/2001 Coupe et al.
2001/0016565 A1 8/2001 Bodet et al.
2002/0012646 A1 1/2002 Royce et al.
2002/0028182 A1 3/2002 Dawson
2002/0037299 A1 3/2002 Turowski-Wanke et al.
2002/0172648 A1 11/2002 Hehner et al.
2002/0193265 A1 12/2002 Perron et al.
2002/0197213 A1 12/2002 Schmenger et al.
2003/0003070 A1 1/2003 Eggers et al.
2003/0008787 A1 1/2003 Mcgee et al.
2003/0022799 A1 1/2003 Alvarado et al.
2003/0049292 A1 3/2003 Turowski-Wanke et al.
2003/0050150 A1 3/2003 Tanaka
2003/0059377 A1 3/2003 Riley
2003/0083210 A1 5/2003 Goldberg
2003/0108501 A1 6/2003 Hofrichter
2003/0147842 A1 8/2003 Restle et al.
2003/0154561 A1 8/2003 Patel
2003/0161802 A1 8/2003 Flammer
2003/0180238 A1 9/2003 Sakurai et al.
2003/0180246 A1 9/2003 Frantz et al.
2003/0185867 A1 10/2003 Kerschner et al.
2003/0192922 A1 10/2003 Ceppaluni et al.
2003/0202952 A1 10/2003 Wells et al.
2003/0223951 A1 12/2003 Geary et al.
2003/0228272 A1 12/2003 Amjad et al.
2004/0014879 A1 1/2004 Denzer et al.
2004/0064117 A1 4/2004 Hammons
2004/0131660 A1 7/2004 Lange et al.
2004/0144863 A1 7/2004 Kendrick
2004/0151793 A1 8/2004 Paspaleeva-Kuhn et al.
2004/0157754 A1 8/2004 Geary et al.
2004/0229963 A1 11/2004 Stephane
2004/0234484 A1 11/2004 Peffly
2004/0235689 A1 11/2004 Sakai et al.
2005/0003975 A1 1/2005 Browne et al.
2005/0003980 A1 1/2005 Baker
2005/0020468 A1 1/2005 Frantz et al.
2005/0136011 A1 6/2005 Nekludoff
2005/0152863 A1 7/2005 Brautigam
2005/0192207 A1 9/2005 Morgan et al.
2005/0201967 A1 9/2005 Albrecht et al.
2005/0202984 A1 9/2005 Schwartz et al.
2005/0208106 A1 9/2005 Lange et al.
2005/0227902 A1 10/2005 Erazo-majewicz et al.
2005/0233929 A1 10/2005 Queen
2005/0245407 A1 11/2005 Ishihara
2005/0276831 A1 12/2005 Dihora
2006/0002880 A1 1/2006 Peffly
2006/0005333 A1 1/2006 Catalfamo et al.
2006/0009337 A1 1/2006 Smith
2006/0030509 A1 2/2006 Modi
2006/0034778 A1 2/2006 Kitano et al.
2006/0057075 A1 3/2006 Arkin et al.
2006/0057097 A1 3/2006 Derici
2006/0079417 A1 4/2006 Wagner
2006/0079418 A1 4/2006 Wagner et al.
2006/0079419 A1 4/2006 Wagner et al.
2006/0079420 A1 4/2006 Wagner et al.
2006/0079421 A1 4/2006 Wagner et al.
2006/0084589 A1 4/2006 Mad et al.
2006/0090777 A1 5/2006 Hecht et al.
2006/0094610 A1 5/2006 Yamato et al.
2006/0110415 A1 5/2006 Gupta
2006/0120982 A1 6/2006 Derici et al.
2006/0120988 A1 6/2006 Bailey et al.
2006/0135397 A1 6/2006 Bissey-beugras
2006/0166857 A1 7/2006 Surburg et al.

(56) References Cited

U.S. PATENT DOCUMENTS

2006/0171911 A1 8/2006 Schwartz et al.
2006/0182703 A1 8/2006 Arisz
2006/0183662 A1 8/2006 Crotty
2006/0210139 A1 9/2006 Carroll
2006/0229227 A1 10/2006 Goldman
2006/0252662 A1 11/2006 Soffin
2006/0263319 A1 11/2006 Fan et al.
2006/0269503 A1 11/2006 Yamazaki
2006/0276357 A1 12/2006 Smith, III et al.
2006/0292104 A1 12/2006 Guskey
2007/0003499 A1 1/2007 Shen et al.
2007/0020263 A1 1/2007 Shitara et al.
2007/0072781 A1 3/2007 Soffin et al.
2007/0110700 A1 5/2007 Wells
2007/0154402 A1 7/2007 Trumbore et al.
2007/0155637 A1 7/2007 Smith et al.
2007/0160555 A1 7/2007 Staudigel
2007/0179207 A1 8/2007 Fernandez de Castro et al.
2007/0225193 A1 9/2007 Kuhlman et al.
2007/0269397 A1 11/2007 Terada
2007/0275866 A1 11/2007 Dykstra
2007/0292380 A1 12/2007 Staudigel
2007/0298994 A1 12/2007 Finke et al.
2008/0003245 A1 1/2008 Kroepke et al.
2008/0008668 A1 1/2008 Harichian et al.
2008/0019928 A1 1/2008 Franzke et al.
2008/0063618 A1 3/2008 Johnson
2008/0138442 A1 6/2008 Johnson
2008/0152610 A1 6/2008 Cajan
2008/0160093 A1 7/2008 Schwartz et al.
2008/0176780 A1 7/2008 Warr
2008/0194454 A1 8/2008 Morgan
2008/0206179 A1 8/2008 Peffly et al.
2008/0229512 A1 9/2008 Syed et al.
2008/0260655 A1 10/2008 Tamarkin et al.
2008/0260665 A1 10/2008 Guerchet et al.
2008/0261844 A1 10/2008 Ruppert et al.
2008/0317698 A1 12/2008 Wells et al.
2009/0005280 A1 1/2009 Woo et al.
2009/0029900 A1 1/2009 Cetti et al.
2009/0041702 A1 2/2009 Molenda
2009/0062406 A1 3/2009 Loeffler
2009/0098076 A1 4/2009 Barg et al.
2009/0155383 A1 6/2009 Kitko et al.
2009/0178210 A1 7/2009 Bistram
2009/0197784 A1 8/2009 Ainger
2009/0221463 A1 9/2009 Kitko et al.
2009/0240223 A1 9/2009 Warren
2009/0246236 A1 10/2009 Kitko
2009/0312223 A1 12/2009 Yang et al.
2009/0312224 A1 12/2009 Yang et al.
2009/0324505 A1 12/2009 Seidling
2010/0000116 A1 1/2010 Aouad et al.
2010/0001116 A1 1/2010 Johnson
2010/0009285 A1 1/2010 Daems et al.
2010/0061946 A1 3/2010 Scherner et al.
2010/0087357 A1 4/2010 Morgan, III et al.
2010/0152083 A1 6/2010 Velazquez
2010/0168251 A1 7/2010 Warr et al.
2010/0183539 A1 7/2010 Bernhardt
2010/0215775 A1 8/2010 Schmaus et al.
2010/0287710 A1 11/2010 Denutte et al.
2010/0310644 A1 12/2010 Liebmann
2010/0322878 A1 12/2010 Stella et al.
2011/0008267 A1 1/2011 Arkin et al.
2011/0023266 A1 2/2011 Gross et al.
2011/0098209 A1 4/2011 Smets et al.
2011/0107524 A1 5/2011 Chieffi et al.
2011/0118691 A1 5/2011 Nishitani
2011/0139170 A1 6/2011 Hippe et al.
2011/0150815 A1 6/2011 Woo et al.
2011/0165107 A1 7/2011 Derks et al.
2011/0171155 A1 7/2011 Federle
2011/0177017 A1 7/2011 Coffindaffer et al.
2011/0232668 A1* 9/2011 Hoffmann ................ A61K 8/44
424/70.13
2011/0245126 A1 10/2011 Tsaur et al.
2011/0245134 A1 10/2011 Smets
2011/0245136 A1 10/2011 Smets
2011/0268778 A1 11/2011 Dihora
2011/0269657 A1 11/2011 Dihora
2011/0300095 A1 12/2011 Dente et al.
2011/0303766 A1 12/2011 Smith
2011/0305739 A1 12/2011 Royce
2011/0305778 A1 12/2011 Caggioni et al.
2011/0308555 A1 12/2011 Smets et al.
2011/0308556 A1 12/2011 Smets et al.
2011/0319790 A1 12/2011 Kost et al.
2012/0004328 A1 1/2012 Huchel et al.
2012/0009285 A1 1/2012 Wei et al.
2012/0014901 A1 1/2012 Sunkel et al.
2012/0031419 A1 2/2012 Batt
2012/0034173 A1 2/2012 Batt
2012/0052031 A1 3/2012 Troccaz et al.
2012/0100091 A1 4/2012 Hata et al.
2012/0100092 A1 4/2012 Murray
2012/0129924 A1 5/2012 Park et al.
2012/0219610 A1 8/2012 Smith, III et al.
2012/0230936 A1 9/2012 Mikkelsen
2012/0237469 A1 9/2012 Dente et al.
2012/0246851 A1 10/2012 Smith, III et al.
2012/0258150 A1 10/2012 Rauckhorst et al.
2012/0291911 A1 11/2012 Smith
2012/0309660 A1 12/2012 Kawasoe
2012/0316095 A1 12/2012 Wei et al.
2013/0029932 A1 1/2013 Kachi et al.
2013/0034515 A1 2/2013 Stone et al.
2013/0043145 A1 2/2013 Smith, III et al.
2013/0043146 A1 2/2013 Smith, III et al.
2013/0043147 A1 2/2013 Smith, III et al.
2013/0045285 A1 2/2013 Stella et al.
2013/0053295 A1 2/2013 Kinoshita et al.
2013/0053300 A1 2/2013 Scheibel et al.
2013/0089587 A1 4/2013 Staudigel
2013/0115173 A1 5/2013 Trumbore et al.
2013/0143784 A1 6/2013 Rizk
2013/0150338 A1 6/2013 Ananthapadmanabhan
2013/0156712 A1 6/2013 Frantz
2013/0189212 A1 7/2013 Jawale et al.
2013/0211952 A1 8/2013 Sugaya
2013/0216491 A1 8/2013 Ogihara et al.
2013/0243718 A1 9/2013 Pasquet
2013/0244922 A1 9/2013 Bartelt
2013/0266642 A1 10/2013 Hollingshead et al.
2013/0280192 A1 10/2013 Carter et al.
2013/0280202 A1 10/2013 Stella et al.
2013/0284195 A1 10/2013 Murdock
2013/0296289 A1 11/2013 Hall et al.
2013/0319463 A1 12/2013 Policicchio
2014/0037703 A1 2/2014 Dihora et al.
2014/0039066 A1 2/2014 Grimadell et al.
2014/0086893 A1 3/2014 Gutmann et al.
2014/0112879 A1 4/2014 Molenda et al.
2014/0127149 A1 5/2014 Lepilleur
2014/0131395 A1 5/2014 Chang
2014/0134125 A1 5/2014 Dahl
2014/0162979 A1 6/2014 Palla-venkata
2014/0171471 A1 6/2014 Krueger
2014/0186864 A1 7/2014 Kato et al.
2014/0201927 A1 7/2014 Bianchetti et al.
2014/0216495 A1 8/2014 Bureiko
2014/0221269 A1 8/2014 Sobel et al.
2014/0228268 A1 8/2014 Fahl et al.
2014/0237732 A1 8/2014 Zuedel Fernandes et al.
2014/0246515 A1 9/2014 Nakajima
2014/0308227 A1 10/2014 Mabille
2014/0309154 A1 10/2014 Carter et al.
2014/0335041 A1 11/2014 Peffly et al.
2014/0348884 A1 11/2014 Hilvert et al.
2014/0348886 A1 11/2014 Johnson et al.
2014/0349902 A1 11/2014 Allef et al.
2015/0017152 A1 1/2015 Potechin et al.
2015/0021496 A1 1/2015 Shabbir

(56) References Cited

U.S. PATENT DOCUMENTS

2015/0037273 A1 2/2015 Wagner
2015/0050231 A1 2/2015 Murase
2015/0057208 A1 2/2015 Frantz et al.
2015/0071977 A1 3/2015 Dihora
2015/0093420 A1 4/2015 Snyder
2015/0093429 A1 4/2015 Carter et al.
2015/0098921 A1 4/2015 Franzke et al.
2015/0099684 A1 4/2015 Boutique
2015/0108163 A1 4/2015 Smith et al.
2015/0110728 A1 4/2015 Jayaswal
2015/0141310 A1 5/2015 Smets et al.
2015/0147286 A1 5/2015 Barrera
2015/0157548 A1 6/2015 De Feij et al.
2015/0218496 A1 8/2015 Schmiedel et al.
2015/0231045 A1 8/2015 Krohn et al.
2015/0262354 A1 9/2015 Periaswamy
2015/0297489 A1 10/2015 Kleinen et al.
2015/0299400 A1 10/2015 Wagner et al.
2015/0306006 A1 10/2015 Aistrup et al.
2015/0313818 A1 11/2015 Stagg
2015/0352027 A1 12/2015 Thomas et al.
2015/0359716 A1 12/2015 Marsh et al.
2015/0359725 A1 12/2015 Glenn, Jr. et al.
2015/0359726 A1 12/2015 Glenn, Jr. et al.
2015/0359728 A1 12/2015 Glenn, Jr. et al.
2016/0001455 A1 1/2016 Swenson
2016/0008257 A1 1/2016 Zhou et al.
2016/0015608 A1 1/2016 Marsh et al.
2016/0022566 A1 1/2016 Figura
2016/0089317 A1 3/2016 Cetti et al.
2016/0089318 A1 3/2016 Cetti et al.
2016/0089322 A1 3/2016 Santos Nogueira et al.
2016/0089462 A1 3/2016 Frankenbach
2016/0089464 A1 3/2016 Frankenbach et al.
2016/0089465 A1 3/2016 Frankenbach et al.
2016/0090555 A1 3/2016 Frankenbach
2016/0090556 A1 3/2016 Frankenbach et al.
2016/0090557 A1 3/2016 Frankenbach et al.
2016/0090558 A1 3/2016 Frankenbach et al.
2016/0092661 A1 3/2016 Hollingshead et al.
2016/0095804 A1 4/2016 Xavier et al.
2016/0113849 A1 4/2016 Grimadell et al.
2016/0128944 A1 5/2016 Chawrai
2016/0193125 A1 7/2016 Jones et al.
2016/0206522 A1 7/2016 Ribaut et al.
2016/0235643 A1 8/2016 Mathonneau et al.
2016/0250115 A1 9/2016 Li et al.
2016/0279048 A1 9/2016 Jayaswal et al.
2016/0287503 A1 10/2016 Schroeder
2016/0287509 A1 10/2016 Peffly
2016/0296656 A1 10/2016 Scavone et al.
2016/0303043 A1 10/2016 Khoury
2016/0306909 A1 10/2016 Hollingshead et al.
2016/0309871 A1 10/2016 Torres Rivera et al.
2016/0310369 A1 10/2016 Thompson et al.
2016/0310370 A1 10/2016 Zhao et al.
2016/0310371 A1 10/2016 Zhao
2016/0310375 A1 10/2016 Torres Rivera
2016/0310386 A1 10/2016 Smith, III et al.
2016/0310388 A1 10/2016 Smith, III et al.
2016/0310389 A1 10/2016 Thompson et al.
2016/0310390 A1 10/2016 Smith, III et al.
2016/0310391 A1 10/2016 Smith, III et al.
2016/0310393 A1 10/2016 Chang et al.
2016/0310402 A1 10/2016 Zhao et al.
2016/0317424 A1 11/2016 Kadir
2016/0326458 A1 11/2016 Smets et al.
2016/0338929 A1 11/2016 Zasloff
2016/0354300 A1 12/2016 Thompson et al.
2016/0374932 A1 12/2016 Song et al.
2017/0066579 A1 3/2017 Zillges
2017/0071837 A1 3/2017 Schelges et al.
2017/0101609 A1 4/2017 Vargas
2017/0110690 A1 4/2017 Lamansky et al.
2017/0110695 A1 4/2017 Nishikawa et al.
2017/0119917 A1 5/2017 Frankenbach et al.
2017/0137752 A1 5/2017 Frankenbach et al.
2017/0137753 A1 5/2017 Frankenbach et al.
2017/0165164 A1 6/2017 Zhao et al.
2017/0165165 A1 6/2017 Zhao et al.
2017/0209359 A1 7/2017 Zhao et al.
2017/0224607 A1 8/2017 Li et al.
2017/0239155 A1 8/2017 Hartnett
2017/0249407 A1 8/2017 Cetti et al.
2017/0249408 A1 8/2017 Cetti et al.
2017/0252273 A1 9/2017 Renock et al.
2017/0255725 A1 9/2017 Frankenbach et al.
2017/0273880 A1 9/2017 Hertenstein
2017/0278249 A1 9/2017 Stofel
2017/0283959 A1 10/2017 Shellef
2017/0304172 A1 10/2017 Chang et al.
2017/0304184 A1 10/2017 Glenn, Jr.
2017/0304185 A1 10/2017 Glenn, Jr. et al.
2017/0304186 A1 10/2017 Glenn, Jr.
2017/0333321 A1 11/2017 Carnali
2017/0333591 A9 11/2017 Scavone et al.
2017/0367963 A1 12/2017 Kadir et al.
2018/0004875 A1 1/2018 Cetti et al.
2018/0044097 A1 2/2018 Zeik
2018/0057451 A1 3/2018 Owens et al.
2018/0066210 A1 3/2018 Frankenbach et al.
2018/0098923 A1 4/2018 Hutton, III
2018/0110594 A1 4/2018 Atkin
2018/0110688 A1 4/2018 Torres Rivera et al.
2018/0110689 A1 4/2018 Torres Rivera et al.
2018/0110690 A1 4/2018 Torres Rivera
2018/0110691 A1 4/2018 Torres Rivera et al.
2018/0110692 A1 4/2018 Torres Rivera et al.
2018/0110693 A1 4/2018 Renock et al.
2018/0110694 A1 4/2018 Renock et al.
2018/0110695 A1 4/2018 Thompson
2018/0110696 A1 4/2018 Johnson et al.
2018/0110704 A1 4/2018 Zhao et al.
2018/0110707 A1 4/2018 Zhao et al.
2018/0110710 A1 4/2018 Zhao et al.
2018/0110714 A1 4/2018 Glenn, Jr. et al.
2018/0116937 A1 5/2018 Park et al.
2018/0116941 A1 5/2018 Wang
2018/0133133 A1 5/2018 Kleinen et al.
2018/0177708 A1 6/2018 Lee et al.
2018/0221266 A1 8/2018 Zhao et al.
2018/0256475 A1 9/2018 Terrisse et al.
2018/0256481 A1 9/2018 Glenn, Jr.
2018/0280270 A1 10/2018 Rughani et al.
2018/0311135 A1 11/2018 Chang
2018/0311136 A1 11/2018 Chang
2018/0318194 A1 11/2018 Hoffmann et al.
2018/0344611 A1 12/2018 Zhao et al.
2018/0344612 A1 12/2018 Zhao et al.
2018/0344613 A1 12/2018 Zhao et al.
2018/0344614 A1 12/2018 Zhao et al.
2018/0360713 A1 12/2018 Jouy et al.
2019/0105242 A1 4/2019 Song
2019/0105243 A1 4/2019 Song
2019/0105244 A1 4/2019 Song
2019/0105245 A1 4/2019 Song
2019/0105246 A1 4/2019 Cochran et al.
2019/0105247 A1 4/2019 Song et al.
2019/0117543 A1 4/2019 Zhao
2019/0117544 A1 4/2019 Zhao
2019/0117545 A1 4/2019 Zhao
2019/0125650 A1 5/2019 Lee et al.
2019/0142711 A1 5/2019 Torres Rivera
2019/0142800 A1 5/2019 Ghosh et al.
2019/0155975 A9 5/2019 Cetti et al.
2019/0167554 A1 6/2019 Wankhade
2019/0183777 A1 6/2019 Gillis
2019/0183778 A1 6/2019 Glenn, Jr.
2019/0192405 A1 6/2019 Zhao
2019/0240121 A1 8/2019 Torres Rivera
2019/0290553 A1 9/2019 Yokogi et al.
2019/0290554 A1 9/2019 Yokogi et al.
2019/0290556 A1 9/2019 Yokogi et al.
2019/0290562 A1 9/2019 Yokogi et al.

(56) References Cited

U.S. PATENT DOCUMENTS

| | | | |
|---|---|---|---|
| 2019/0290567 | A1 | 9/2019 | Yokogi et al. |
| 2019/0290568 | A1 | 9/2019 | Yokogi et al. |
| 2019/0307298 | A1 | 10/2019 | Zhao |
| 2019/0307665 | A1 | 10/2019 | Yokogi et al. |
| 2019/0328647 | A1 | 10/2019 | Chang et al. |
| 2019/0365611 | A1 | 12/2019 | Brown et al. |
| 2019/0365619 | A1 | 12/2019 | Ceballos et al. |
| 2019/0365633 | A1 | 12/2019 | Glenn, Jr. |
| 2020/0000690 | A1 | 1/2020 | Renock |
| 2020/0078284 | A1 | 3/2020 | Botto et al. |
| 2020/0113796 | A1 | 4/2020 | Yokogi |
| 2020/0129402 | A1 | 4/2020 | Jamadagni |
| 2020/0163846 | A1 | 5/2020 | Song |
| 2020/0163860 | A1 | 5/2020 | Adamy et al. |
| 2020/0170894 | A1 | 6/2020 | Park et al. |
| 2020/0197272 | A1 | 6/2020 | Hertenstein et al. |
| 2020/0206110 | A1 | 7/2020 | Hertenstein et al. |
| 2020/0237628 | A1 | 7/2020 | Torres Rivera |
| 2021/0022986 | A1 | 1/2021 | Glenn, Jr. |
| 2021/0093543 | A1 | 4/2021 | Parikh et al. |
| 2021/0121385 | A1 | 4/2021 | Muller et al. |
| 2021/0128444 | A1 | 5/2021 | Muller et al. |
| 2021/0128447 | A1 | 5/2021 | Galpin et al. |
| 2021/0169765 | A1 | 6/2021 | Renock |
| 2021/0212927 | A1 | 7/2021 | Hutton, III et al. |
| 2021/0267853 | A1 | 9/2021 | Johnson et al. |
| 2021/0275410 | A1 | 9/2021 | Hutton |
| 2021/0353518 | A1 | 11/2021 | Ballhaus et al. |
| 2021/0353522 | A1 | 11/2021 | Ballhaus et al. |
| 2021/0401716 | A1 | 12/2021 | Gogineni et al. |
| 2022/0062136 | A1 | 3/2022 | Feng |
| 2022/0160606 | A1 | 5/2022 | Renock |
| 2022/0175640 | A1 | 6/2022 | Herteinstein et al. |
| 2022/0323337 | A1 | 10/2022 | Yamazaki |
| 2022/0378680 | A1 | 12/2022 | Ballhaus et al. |
| 2022/0378684 | A1 | 12/2022 | Cochran et al. |
| 2022/0395444 | A1 | 12/2022 | Hutton, III |
| 2023/0053056 | A1 | 2/2023 | Renock et al. |
| 2023/0113440 | A1 | 4/2023 | Cochran et al. |
| 2023/0113844 | A1 | 4/2023 | Cochran et al. |
| 2023/0114446 | A1 | 4/2023 | Cochran et al. |
| 2023/0114939 | A1 | 4/2023 | Cochran |
| 2023/0118201 | A1 | 4/2023 | Cochran |
| 2023/0125210 | A1 | 4/2023 | Cochran |
| 2023/0190606 | A1 | 6/2023 | Johnson |
| 2024/0156700 | A1 | 5/2024 | Yokogi |
| 2024/0277598 | A1 | 8/2024 | Brown et al. |
| 2025/0009612 | A1 | 1/2025 | Braganza et al. |

FOREIGN PATENT DOCUMENTS

| | | | |
|---|---|---|---|
| CA | 704195 | A | 2/1965 |
| CA | 1248458 | A | 1/1989 |
| CA | 2078375 | A1 | 3/1994 |
| CN | 1263455 | A | 8/2000 |
| CN | 1286612 | A | 3/2001 |
| CN | 1545404 | A | 11/2004 |
| CN | 1823929 | A | 8/2006 |
| CN | 100534415 | C | 9/2009 |
| CN | 101112349 | B | 5/2011 |
| CN | 101690697 | B | 10/2011 |
| CN | 101559034 | B | 1/2013 |
| CN | 102895151 | A | 1/2013 |
| CN | 102973437 | A | 3/2013 |
| CN | 102697668 | B | 8/2013 |
| CN | 103356408 | A | 10/2013 |
| CN | 102697670 | B | 7/2014 |
| CN | 104107401 | A | 10/2014 |
| CN | 102851015 | B | 12/2014 |
| CN | 105726393 | A | 7/2016 |
| CN | 105769617 | A | 7/2016 |
| CN | 106659664 | A | 5/2017 |
| CN | 106750361 | A | 5/2017 |
| CN | 107595657 | A | 1/2018 |
| CN | 107595673 | A | 1/2018 |
| CN | 107648096 | A | 2/2018 |
| CN | 107737329 | A | 2/2018 |
| CN | 107961212 | A | 4/2018 |
| CN | 108186385 | A | 6/2018 |
| CN | 108283583 | A | 7/2018 |
| CN | 108451858 | A | 8/2018 |
| CN | 110279591 | A | 9/2019 |
| CN | 113041184 | A | 6/2021 |
| DE | 2145204 | A1 | 3/1973 |
| DE | 3018456 | A1 | 11/1981 |
| DE | 4315396 | A1 | 11/1994 |
| DE | 102004012009 | A1 | 9/2005 |
| DE | 202005009618 | U1 | 9/2005 |
| DE | 102004023720 | A1 | 12/2005 |
| DE | 102014225083 | A1 | 10/2015 |
| DE | 102014225606 | A1 | 10/2015 |
| DE | 102015204987 | A1 | 9/2016 |
| EP | 0108517 | A2 | 5/1984 |
| EP | 0574086 | A2 | 12/1993 |
| EP | 0666358 | A1 | 8/1995 |
| EP | 0674898 | A2 | 10/1995 |
| EP | 1340485 | A2 | 2/2003 |
| EP | 1346720 | A2 | 9/2003 |
| EP | 0674898 | B2 | 3/2006 |
| EP | 1714678 | A1 | 10/2006 |
| EP | 1842572 | A2 | 10/2007 |
| EP | 2005939 | A1 | 12/2008 |
| EP | 1970045 | A3 | 9/2009 |
| EP | 2042216 | B1 | 9/2015 |
| EP | 3121210 | A1 | 1/2017 |
| EP | 3260171 | A1 | 12/2017 |
| EP | 3622946 | A1 | 3/2020 |
| ES | 2052450 | B1 | 12/1994 |
| FR | 2669531 | A1 | 5/1992 |
| FR | 2795955 | A1 | 1/2001 |
| GB | 190110699 | A | 8/1901 |
| GB | 191023922 | A | 10/1911 |
| GB | 1347950 | A | 2/1974 |
| GB | 2048229 | | 12/1980 |
| GB | 2450727 | A | 1/2009 |
| HU | 42318 | | 7/1987 |
| JP | S56011009 | A | 12/1981 |
| JP | S58113300 | A | 7/1983 |
| JP | S58198412 | A | 11/1983 |
| JP | S60004598 | A | 1/1985 |
| JP | S61236708 | A | 10/1986 |
| JP | S62205200 | A | 9/1987 |
| JP | S63501221 | A | 5/1988 |
| JP | S63165308 | A | 7/1988 |
| JP | H04364114 | A | 12/1992 |
| JP | H06220495 | A | 8/1994 |
| JP | H0753340 | A | 2/1995 |
| JP | 07252134 | A | 10/1995 |
| JP | H08310924 | A | 11/1996 |
| JP | 09020618 | A | 1/1997 |
| JP | 09030938 | A | 2/1997 |
| JP | H09175961 | A | 7/1997 |
| JP | H10017894 | A | 1/1998 |
| JP | H11139944 | A | 5/1999 |
| JP | 2964226 | B2 | 10/1999 |
| JP | 2000178586 | A | 6/2000 |
| JP | 3069802 | B2 | 7/2000 |
| JP | 2001011492 | A | 1/2001 |
| JP | 2001011497 | A | 1/2001 |
| JP | 2001254099 | A | 9/2001 |
| JP | 2001261529 | A | 9/2001 |
| JP | 2003201217 | A | 12/2001 |
| JP | 2002179552 | A | 6/2002 |
| JP | 2002226889 | A | 8/2002 |
| JP | 2002285191 | A | 10/2002 |
| JP | 2002336337 | A | 11/2002 |
| JP | 2003055699 | A | 2/2003 |
| JP | 2003082398 | A | 3/2003 |
| JP | 2003171688 | A | 6/2003 |
| JP | 2003176497 | A | 6/2003 |
| JP | 2003261413 | A | 9/2003 |
| JP | 2003268398 | A | 9/2003 |
| JP | 3480165 | B2 | 12/2003 |
| JP | 2003342131 | A | 12/2003 |

(56) References Cited

FOREIGN PATENT DOCUMENTS

| | | | |
|---|---|---|---|
| JP | 3634988 | B2 | 3/2005 |
| JP | 3634991 | B2 | 3/2005 |
| JP | 3634996 | B2 | 3/2005 |
| JP | 2005187359 | A | 7/2005 |
| JP | 2005232113 | A | 9/2005 |
| JP | 2006063044 | A | 3/2006 |
| JP | 2006104149 | A | 4/2006 |
| JP | 2006124312 | A | 5/2006 |
| JP | 2006183039 | A | 7/2006 |
| JP | 2006193549 | A | 7/2006 |
| JP | 2006249092 | A | 9/2006 |
| JP | 2006282565 | A | 10/2006 |
| JP | 2007131687 | A | 5/2007 |
| JP | 2007177047 | A | 7/2007 |
| JP | 2007223935 | A | 9/2007 |
| JP | 2007238607 | A | 9/2007 |
| JP | 2007297380 | A | 11/2007 |
| JP | 2008001626 | A | 1/2008 |
| JP | 2008214292 | A | 9/2008 |
| JP | 2009096778 | A | 5/2009 |
| JP | 2009120559 | A | 6/2009 |
| JP | 2009161866 | A | 7/2009 |
| JP | 2010138130 | A | 6/2010 |
| JP | 2011153167 | A | 8/2011 |
| JP | 2011190221 | A | 9/2011 |
| JP | 2011241353 | A | 12/2011 |
| JP | 5041113 | B2 | 7/2012 |
| JP | 2013010757 | A | 1/2013 |
| JP | 2013091641 | A | 5/2013 |
| JP | 2013151434 | A | 8/2013 |
| JP | 2013155143 | A | 8/2013 |
| JP | 2013193968 | A | 9/2013 |
| JP | 2013216639 | A | 10/2013 |
| JP | 6046394 | B2 | 1/2014 |
| JP | 2014009177 | A | 1/2014 |
| JP | 2014024875 | A | 2/2014 |
| JP | 2014037383 | A | 2/2014 |
| JP | 2014091723 | A | 5/2014 |
| JP | 2014234350 | A | 12/2014 |
| JP | 5667790 | B2 | 2/2015 |
| JP | 2015034157 | A | 2/2015 |
| JP | 2015101545 | A | 6/2015 |
| JP | 2015129099 | A | 7/2015 |
| JP | 2016013973 | A | 1/2016 |
| JP | 2016030722 | A | 3/2016 |
| JP | 2016088910 | A | 5/2016 |
| JP | 6184550 | B1 | 8/2017 |
| JP | 2018012673 | A | 1/2018 |
| JP | 2018083781 | A | 5/2018 |
| JP | 2018172315 | A | 11/2018 |
| JP | 7179324 | B2 | 11/2022 |
| KR | 100290589 | B1 | 9/2001 |
| KR | 100821846 | B1 | 4/2008 |
| KR | 1020080111280 | A | 12/2008 |
| KR | 20090095359 | A | 9/2009 |
| KR | 20100040180 | A | 4/2010 |
| KR | 20140060882 | A | 5/2014 |
| KR | 101494008 | B1 | 2/2015 |
| KR | 101503922 | B1 | 3/2015 |
| KR | 101532070 | B1 | 7/2015 |
| UA | 50333 | U | 5/2010 |
| WO | 8603679 | A1 | 7/1986 |
| WO | 9114759 | A1 | 10/1991 |
| WO | 91017237 | A1 | 11/1991 |
| WO | 9213520 | A1 | 8/1992 |
| WO | 199325650 | A1 | 12/1993 |
| WO | 9417783 | A2 | 8/1994 |
| WO | 9502389 | A2 | 1/1995 |
| WO | 9726854 | A1 | 7/1997 |
| WO | 9823258 | A1 | 6/1998 |
| WO | 9906010 | A2 | 2/1999 |
| WO | 9918928 | A1 | 4/1999 |
| WO | 9924004 | A1 | 5/1999 |
| WO | 9924013 | A1 | 5/1999 |
| WO | 9949837 | A1 | 10/1999 |
| WO | 9957233 | A1 | 11/1999 |
| WO | 0012553 | A1 | 3/2000 |
| WO | 0032601 | | 6/2000 |
| WO | 0119949 | A1 | 3/2001 |
| WO | 0142409 | A1 | 6/2001 |
| WO | 0148021 | A1 | 7/2001 |
| WO | 2001076552 | A2 | 10/2001 |
| WO | 2003051319 | A1 | 6/2003 |
| WO | 03096998 | A1 | 11/2003 |
| WO | 03105793 | A2 | 12/2003 |
| WO | 2004078901 | A1 | 9/2004 |
| WO | 2005023975 | A1 | 3/2005 |
| WO | 2008017540 | A1 | 2/2008 |
| WO | 2008128826 | A1 | 10/2008 |
| WO | 2008145582 | A1 | 12/2008 |
| WO | 2009016555 | A2 | 2/2009 |
| WO | 2009030594 | A1 | 3/2009 |
| WO | 2009053931 | A2 | 4/2009 |
| WO | 2010026009 | A1 | 3/2010 |
| WO | 2010052147 | A2 | 5/2010 |
| WO | 2011124560 | A2 | 10/2011 |
| WO | 2012017091 | A2 | 2/2012 |
| WO | 2012052536 | A2 | 4/2012 |
| WO | 2012055587 | A1 | 5/2012 |
| WO | 2012055812 | A1 | 5/2012 |
| WO | 2012084970 | A1 | 6/2012 |
| WO | 2012127009 | A1 | 9/2012 |
| WO | 2012136651 | A1 | 10/2012 |
| WO | 2013010706 | A2 | 1/2013 |
| WO | 2013018805 | A1 | 2/2013 |
| WO | 2013119908 | A1 | 8/2013 |
| WO | 2014073245 | A1 | 5/2014 |
| WO | 2014073456 | A1 | 5/2014 |
| WO | 2014111667 | A2 | 7/2014 |
| WO | 2014111668 | A2 | 7/2014 |
| WO | 2014148245 | A1 | 9/2014 |
| WO | 2015016037 | A1 | 2/2015 |
| WO | 2015067779 | A1 | 5/2015 |
| WO | 2015085376 | A1 | 6/2015 |
| WO | 2015122371 | A1 | 8/2015 |
| WO | 2015141787 | A1 | 9/2015 |
| WO | 2016049389 | A1 | 3/2016 |
| WO | 2016147196 | A1 | 9/2016 |
| WO | 2016178660 | A1 | 11/2016 |
| WO | 2017052161 | A1 | 3/2017 |
| WO | 2017140798 | A1 | 8/2017 |
| WO | 2017140802 | A1 | 8/2017 |
| WO | 2017207685 | A1 | 12/2017 |
| WO | 2018023180 | A1 | 2/2018 |
| WO | 2018064511 | A1 | 4/2018 |
| WO | 2018109148 | A1 | 6/2018 |
| WO | 2019030458 | A2 | 2/2019 |
| WO | 2019074990 | A1 | 4/2019 |
| WO | 2019074992 | A1 | 4/2019 |
| WO | 2019200027 | A1 | 10/2019 |
| WO | 2020005309 | A1 | 1/2020 |
| WO | 2020030732 | A1 | 2/2020 |
| WO | 2020076881 | A1 | 4/2020 |
| WO | 2020131836 | A1 | 6/2020 |
| WO | 2021026572 | A1 | 2/2021 |
| WO | 2021099088 | A1 | 5/2021 |
| WO | 2021127318 | A1 | 6/2021 |
| WO | 2021144326 | A1 | 7/2021 |
| WO | 2021231510 | A1 | 11/2021 |
| WO | 2022144161 | A1 | 7/2022 |
| WO | 2024037872 | A1 | 2/2024 |

OTHER PUBLICATIONS

"Foam & chemical contamination in waterways", Retrieved From https://www.epa.nsw.gov.au/-/media/epa/corporate-site/resources/epa/foam-chemical-contamination-in-waterway.pdf, Dec. 2015, 2 Pages.

"Jaguar® Optima", Solvay, site: www.solvay.com, year 2023, 1 page.

"Natural Detangling Shampoo", Mintel Database, dated Sep. 13, 2017; 2 pages.

"Personal care solutions Guide", Solvay, Publication date: May 2018, 84 pages.

(56) References Cited

OTHER PUBLICATIONS

"Soda Shampoo", Mintel Database, dated Apr. 2015; pp. 1-4.
"Treatment Foam for Recurrent Scaling Conditions", Mintel Database, Aug. 2007; pp. 1-2.
PCT Search Report and Written Opinion for PCT/US2018/055106 dated Jan. 16, 2019, 11 pages.
Third Party Observation for 18796212.1-1112 dated Apr. 1, 2021, 4 pages.
Third Party Observation for 18796212.1-1112 dated Aug. 4, 2021, 4 pages.
Third Party Opposition for 18796212.1 dated Dec. 6, 2022, 10 pages.
Third Party Opposition for 18796212.1 dated Sep. 25, 2020, 6 pages.
Acne Foaming Cleanser, Database accession No. 4172863, Jul. 29, 2016, 3 pages.
Air Quality of the Iowa Department of Natural Resources. A Review of The Science and Technology of Odor Measurement, 2005, 51 pages (2005).
All Office Actions; U.S. Appl. No. 16/156,066, filed Oct. 10, 2018.
All Office Actions; U.S. Appl. No. 16/156,072, filed Oct. 10, 2018.
All Office Actions; U.S. Appl. No. 17/147,574, filed Jan. 13, 2021.
All Office Actions; U.S. Appl. No. 17/320,379, filed May 14, 2021.
All Office Actions; U.S. Appl. No. 17/320,391, filed May 14, 2021.
All Office Actions; U.S. Appl. No. 17/986,044, filed Nov. 14, 2022.
All Office Actions; U.S. Appl. No. 18/083,741, filed on Dec. 19, 2022.
All Office Actions; U.S. Appl. No. 18/609,690, filed on Mar. 19, 2024.
Anonymous, "Healing + Anti-Breakage Shampoo", ID# 3383875, Mintel GNPD, URL: http://www.gnpd.com, dated Aug. 2015, 3 pages.
Anonymous, "Medicated Cleanser", Nioxin Research Laboratories, Mintel GNPD [online], ID:1060983, Url: http://www.gnpd.com, dated Feb. 2009, 4 pages.
Anonymous, "Shampoo", ID# 1743027, Mintel GNPD, URL: http://www.gnpd.com, dated Mar. 2012, 3 pages.
Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018 ; 1 page.
Anonymous: "Anti-Dandruff Scalp Care Shampoo", MINTEL, Database accession No. 301924, Sep. 16, 2004, 2 pages.
Anonymous: "Anticaspa-Graso Anti-Dandruff Shampoo", Database GNPD [Online] Mintel; XPC:155787029, Database accession No. 351776 paragraph [ingredients], Apr. 5, 2005 (Apr. 5, 2005).
Anonymous: "Naturally Derived Body Wash", Database GNPD [Online] MINTEL; Feb. 15, 2021, 2 pages.
Anonymous: "Peptide Shampoo", Database GNPD [Online] MINTEL; Dec. 14, 2015, 3 pages.
Anonymous: "Replenishing Moisture Shampoo", Database GNPD [Online] MINTEL, Mar. 10, 2015.
Anonymous: "Shampoo", Database GNPD [Online] MINTEL, Jan. 26, 2021, 3 pages.
Anonymous: "Shampooing au Phytolait d'abricot—Formule N°102-MP06-MI3-AA03", Internet Citation, Feb. 19, 2005, Retrieved from the Internet: URL: http://web.archive.org/web/20050219040350/www.albanmuller.com/francais/catalogue/formules/formul10.asp, 1 page.
Anonymous; "Advanced Oil Control Anti Dandruff Shampoo", XP093149356, Database GNPD Mintel, Database accession No. 9347772, dated Feb. 1, 2022, 03 Pages.
Anonymous; "Shampoo", ID: 7162235, Database GNPD [Online] MINTEL; dated Jan. 6, 2020, 3 pages.
ASTM D3954-94, Reapproved 2010, vol. 15.04, Standard Test Method for Dropping Point of Waxes.
BASF, "Practical Guide to Rheology Modifiers", download from https://insights.basf.com/files/BASF_ED_RheologyModifiers_download.pdf on Nov. 1, 2022. (Year: 2022).
Brattoli et al. Odour Detection Methods: Olfactometry and Chemical Sensors. Sensors (Basel), 2011; 11(5); 5290-5322 (2011).
Cafasso, "What's the proper order to use shampoo and conditioner while bathing", Healthline, Retrieved from Internet: https://www.healthline.com/health/beauty-skin-care/shampoo-or-conditioner-first, dated Jul. 13, 2020, 2 pages.
Carbopol Aqua SF-1 Polymer Technical Data Sheet, TDS-294, dated Dec. 2000 ; pp. 1-9.
Chemical Book, Isolongifolone, available at http://www.chemicalbook.com/ProductChemicalPropertiesCB5318980_EN.htm, Copyright 2016, 1 page.
Christensen et al., "Experimental Determination of Bubble Size Distribution in a Water col. by Interferometric Particle Imaging and Telecentric Direct Image Method", Student Report, Aalborg University; dated Jun. 3, 2014; 123 pages.
Crepaldi, E.L., et al., Chemical, Structural, and Thermal Properties of Zn(II)-Cr(III) Layered Double Hydroxides Intercalated with Sulfated and Sulfonated Surfactants, Journal of Colloid and Interface Science, 2002, pp. 429-442, vol. 248.
D'Souza et al., Shampoo and Conditioners: What a Dermatologist Should Know? Indian J Dermatol, dated May-Jun. 2015; p. 60(3), 248-254 (2015).
Database GNPD [Online] MINTEL; Mar. 28, 2018 (Mar. 28, 2018), anonymous: Dandruff Control Shampoo 11, XP055787038, Database accession No. 5556267, abstract.
Database WPI; Week 201459; Thomson scientific, London, GB; an 2014-P66521; XP002752638; 2 pages. (No known date).
Datasheet: Empigen Total Active TC/U, Datasheet, dated Jan. 31, 2017 (Innospec) ; 2 pages.
Dehyquart Guar: Published dated Nov. 2010 ; pp. 1-34.
Duis et al., "Environmental fate and effects of water-soluble synthetic organic polymers used in cosmetic products", Enviromental Sciences Europe, 33:21, Year 2021; 20 pages.
Fevola, Michael J. "Guar Hydroxypropyltrimonium Chloride." Cosmetics and toiletries; vol. 127.1; Jan. 2012 ; pp. 16-21.
Grillet et al., "Polymer Gel Rheology and Adhesion", Rheology, 2012, pp. 59-80.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018; p. 1.
Happi: "Sulfate-Free Surfactants Conditioning Shampoo", Retrieved from the Internet: URL:https://www.happi.com/contents/view_formulary/2009-10-01/sulfate-free-surfactants-conditioning-shampoo/, XP002804301, Jan. 10, 2019, 1 page.
Inspection certificate for Hostapon® CCG, Clariant Ibérica Production, S.A., May 6, 2019; p. 1-2.
Manuel, F. et al., "A new postulate on two stages of dandruff": A clinical perspective, International Journal of Trichology, 2011, vol. 3, 3-6 (Year: 2011).
Matsouka et al., "Vesicle formation of disodium lauryl sulfosuccinate", Journal of Molecular Liquids, 348, 118422, Nov. 1, 2021, 7 pages.
McGinley et al., "Performance Verification of Air Freshener Products and Other Odour Control Devices for Indoor Air Quality Malodours", Presented at the 8th Workshop on Odour and Emissions of Plastic Materials Universitat Kassel Institut for Wesrkstofftechnik Kassel, Germany, Mar. 27-28, 2006, 13 pages.
McGinley et al., American Association of Textile Chemists and Colorists, year 2017, 16 pages.
Medvedev, Diffusion Coefficients in Multicomponent Mixtures, PhD Thesis from Technical University of Denmark, dated 2005, 181 pages.
Mintel GNPD Base, Bright Blonde Shampoo Record No. 3412889 Feb. 29, 2016 ; 2 pages.
Mintel GNPD Base, Mineral Conquer Blonde Silver Shampoo Record No. 3953107 Apr. 30, 2016; 2 pages.
Mintel GNPD Base, Royal Treatment Collection, Record No. 1946223 dated Dec. 31, 2011, 3 pages.
Morioka, H. et al. "Effects of Zinc on the New Preparation Method of Hydroxy Double Salts" Inorg. Chem. 1999, 38, 4211-6.

(56) References Cited

OTHER PUBLICATIONS

Musazzi, "Emulsion versus nonoemulsion: how much is the formulative shift critical for a cosmetic product?" (Drug Deliv. and Trans. Res. (2018) 8: pp. 414-421 (Year: 2018).
Natural oils: why specific carbon chains are chosen for certain surfactant properties, Chemlink, URL Link: https://www.chemlink.co.uk/natural-oils-why-specific-carbon-chains-are-chosen-for-certain-surfactant-properties/a (Year: 2022), 4 pgs.
Naturally Rich Moisturizing Shampoo, Database accession No. 6421011, Mar. 27, 2019, 3 pages.
Noritomi H. Formation and Solubilization Property of Water-in-Oil Microemulsions of Alkyl Glucoisdes. Advances in Nanoparticles, 2013, 2, 366-371 (Year: 2013).
P. A. Cornwell, "A review of shampoo surfactant technology: consumer benefits, raw materials and recent developments", International Journal of Cosmetic Science, 40 , Oct. 27, 2017, pp. 16-30.
Parchem fine & specialty chemicals. MIPA-laureth sulfate supplier distributor—CAS 83016-76-6; dated 2021; pp. 1-7.
PERM Inc, , Diffusion Coefficient: Measurement Techiques, https://perminc.com/resources/fundamentals-of-fluid-flow-in-porous-media/chapter-3-molecular-diffusion/diffusion-coefficient/measurement-techniques, dated Oct. 2020; p. 1-4.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-the Safety-Assessment-of-Polyquaternium-10.pdf, retrieved on Dec. 20, 2018; 9 pages.
Practical Modern Hair Science, Published 2012; 43 pages.
Product Bulletin, Amphosol® CG, Cocamidopropyl Betaine, Stepan Company, Jun. 2011; 1-2 pages.
Product Data Record Tego®Betain F Kb 5, dated Jul. 1, 2015, 4 pages.
Product Data Sheet for Chemoryl LS Surfactant, Sodium Lauroyl Sarcosinate, Lubrizol Advanced Materials, Inc., Mar. 24, 2020; 1-2 pages.
Product Data Sheet, Eversoft UCS-40S, Disodium Cocoyl Glutamate (Sodium Cocoyl Glutamate*), Sino Lion USA, Jul. 2018; 2 pages.
Product Fact Sheet—Hostapon® CCG, mild anionic surfactant for the cosmetic industry, Clariant International Ltd., Aug. 2014 ; 1-3 pages.
Product Fact Sheet, Hostapon® CGN, Mild anionic surfactant for the cosmetic industry, Clariant International Ltd., Jan. 2016; 1-2 pages.
PubChem CID 3033856 for decyl glucoside. downloaded Jun. 22, 2023, 32 pages. (Year: 2023).
Rajendran A. et al: "Study on the Analysis of Trace Elements in Aloevera and Its Biological Importance Study on the Analysis of Trace Elements in Aloe vera and Its Biological Importance", Journal of Applied Sciences Research, Jan. 1, 2007 (Jan. 1, 2007), pp. 1476-1478.
Ramachandra et al., "Processing of Aloe Vera Leaf Gel: A Review", American Journal of Agricultural and Biological Sciences 3 (2), year 2008, pp. 502-510.
Robinson et al., Final Report of the Amended Safety Assessment of Sodium Laureth Sulfate and Related Salts of Sulfated Ethoxylated Alcohols, International Journal of Toxicology 29 (Supplement 3); dated 2010; pp. 151S-161S.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, dated Nov. 1, 2008, pp. 304-308, p. 305—left-hand column; 3 pages.
Safety assessment of amino acid alkyl amides used in cosmetics , dated Sep. 20, 2013, 46 pages.
Sbhatu et al., "Formulation and Physicochemical Evaluation of Lab-Based Aloe adigratana Reynolds Shampoos", Hindawi, International Journal of Analytical Chemistry, vol. 2020, Article ID 6290617, URL: https://www.ncbi.nlm.nih.gov/pmc/articles/PMC7160718/, Published Apr. 4, 2020, 7 pages.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012; 1-2 pages.
Sensory., "A Review of The Science and Technology of Odor Measurement", Prepared for the Air Quality Bureau of the Iowa Department of Natural Resources, Dec. 30, 2005 51 pages.
Shampoo C, Database accession No. 1632217, Sep. 29, 2011, 3 pages.
Shampoo Manufacturing Plant, Lodha International, URL: https://www.lodhapharma.com/shampoo-manufacturing-plant.php#: ~:text=Shampoos%20are%20categorized%20as%20viscous,if%20not%20all%20of%20them, Published: 2018, 4 pages.
Shampoo, ID# 6148479, Mintel GNPD [online], URL: http://www.gnpd.com, Nov. 2018, 4 pages.
Softazoline CL-R, Kawaken Singapore PTE Ltd. Website printout from http://kawaken.com.sg/softazoline-ch-r//a, accessed on Nov. 30, 2022.
Technical Information; TEGO® Betain F Kb 5 / TEGO® Betain F KM 1; Mild amphoteric surfactants: www.evonik.com/personal-care; Jul. 2010; 2 pages; Product Specification; 5 pages.
Todd et al., Volatile Silicone Fluids for Cosmetics, Cosmetics and Toiletries, vol. 91, pp. 27-32 (Jan. 1976).
UL Prospector® Product Data Sheet, Plantacare® 818 UP, C8-16 fatty alcohol glucoside, BASF, dated May 21, 2015; 1-3 pages.
Unhale Shri krushna Subhash et al: Formulation and Development of Sulphate Free Shampoo About an Updates and Guidelines of Corona Virus View project health and beauty science View project Rohit Bhavsar Reliance Industries Limited; International Journal for Research inApplied Science & Engineering Technology, Apr. 1, 2020 (Apr. 1, 2020) XP055842327, DOI: 10.22214, 14 pages.
Yang et al., "Synthesis and foaming performance of Lauramidopropyl Betaine Derivate Surfactants", Materials Science Forum, vol. 953, Jan. 9, 2019, 1 page.
"Deep Image Matting", Ning Xu et al., Beckman Institute for Advanced Science and Technology, University of Illinois at Urbana-Champaign, Adobe Research, dated Mar. 10, 2017; 10 pages.

* cited by examiner

SULFATE FREE PERSONAL CLEANSING COMPOSITION COMPRISING LOW INORGANIC SALT

FIELD OF THE INVENTION

The present disclosure generally relates to stable, sulfate-free personal cleansing compositions formulated with an acyl taurate anionic surfactant, a cationic deposition polymer and little or no inorganic salt and, optionally, an amphoteric surfactant.

BACKGROUND OF THE INVENTION

Most commercial cleansing compositions, such as shampoo compositions, comprise sulfate-based surfactant systems because of their effectiveness in generating high lather volume and good lather stability and cleaning. However, some consumers may prefer a shampoo composition that is substantially free of sulfate-based surfactant systems. In addition, sulfate free shampoos users prefer high conditioning shampoos because higher conditioning shampoos feel less stripping to the hair. Conditioning shampoos based on sulfate based surfactant systems typically contain cationic conditioning polymers to form coacervate with the sulfate based surfactant system during use. However, it can be difficult to use non-sulfate based surfactants in liquid shampoos because it can be difficult to formulate a composition that has acceptable lather volume, cleansing, conditioning benefit, stability. One common problem is that using certain cationic conditioning polymers in products that are substantially free of sulfate containing surfactants can result in instability. In particular, a second phase known as surfactant-polymer coacervate can be formed in the composition (rather than the desired formation during use) as the result of interaction between the cationic polymer and the non-sulfate anionic surfactants. This is observed by the consumer as a cloudy product or a product with a precipitated layer, which is not consumer preferred. Presence of coacervate in the cleaning compositions can lead to separation upon storage, causing inconsistent performance in use. Thus, there is a need to formulate stable shampoo products comprising anionic non-sulfated surfactants, amphoteric surfactant and cationic polymers without forming the coacervate phase in the product, yet a coacervate is formed when diluted with water during use, such as during shampooing, delivering desired wet conditioning benefits on hair. There is also a need to be able to formulate versions of these products without the use of a rheology modifier or a thickener. This need is even more important for products that have low viscosity, such as foamed products delivered via an aerosol device or a mechanical former, such as a pump. The viscosity of such compositions may be significantly lower than the typical liquid shampoos.

It has been surprisingly found that stable products that exhibit good spreadability and good conditioning can be achieved.

SUMMARY OF THE INVENTION

The present disclosure relates to a cleansing composition comprising about 3 wt % to about 35 wt % of an acyl taurate anionic surfactant; about 3 wt % to about 15% of an amphoteric surfactant; about 0.01 wt % to about 2 wt % of a cationic polymer having a weight average molecular weight of 300,000 g/mol to about 3,000,000 g/mol; 0 wt % to about 1.0 wt % of inorganic salts; and an aqueous carrier. The composition is substantially free of sulfate-based surfactant and does not form a coacervate prior to use.

DETAILED DESCRIPTION OF THE INVENTION

While the specification concludes with claims particularly pointing out and distinctly claiming the invention, it is believed that the present disclosure will be better understood from the following description.

As used herein, the term “fluid” includes liquids and gels.

As used herein, the articles including “a” and “an” when used in a claim, are understood to mean one or more of what is claimed or described.

As used herein, “comprising” means that other steps and other ingredients which do not affect the end result can be added. This term encompasses the terms “consisting of” and “consisting essentially of”.

As used herein, “mixtures” is meant to include a simple combination of materials and any compounds that may result from their combination.

As used herein, “molecular weight” or “M.Wt.” refers to the weight average molecular weight unless otherwise stated. Molecular weight is measured using industry standard method, gel permeation chromatography (“GPC”). The molecular weight has units of grams/mol.

As used herein, “cleansing composition” includes personal cleansing products such as shampoos, conditioners, conditioning shampoos, shower gels, liquid hand cleansers, facial cleansers, and other surfactant-based liquid compositions.

As used herein, the terms “include,” “includes,” and “including,” are meant to be non-limiting and are understood to mean “comprise,” “comprises,” and “comprising,” respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Cleansing Compositions

Typically, inorganic salt is added to sulfated surfactant based cleansing formulations to thicken the product. It has been surprisingly found that adding inorganic salt to the formulas that are substantially free of sulfate containing surfactants and/or using high inorganic salt containing sulfate free surfactants in the presence of cationic conditioning polymer can cause product instability due to formation of a gel-like surfactant-polymer complex known as coacervate in the composition. By maintaining low inorganic salt concentration in formulas (from about 0 to about 1 wt %) the instability issue in sulfate free formulations comprising anionic surfactant and high molecular weight cationic polymer is resolved. The inorganic salt can include sodium chloride, potassium chloride, sodium sulfate, ammonium chloride, sodium bromide, and combinations thereof. The solution is to avoid or minimize adding extra inorganic salt to the formula and/or by using low inorganic salt containing raw materials. For example, commercially available sulfate free surfactants such as disodium cocoyl glutamate typically comes with high levels of inorganic salt such as 5% or higher. Amphoteric surfactant such as betaines or sultaines also typically come with high levels of inorganic salt such as NaCl. Use of these high salt containing raw materials in sulfate-free surfactant based cleaning formulations in excess of about 1% total NaCl in the formulation can cause formation of undesired coacervate in the product. If the inorganic salt level is lowered in the surfactant raw materials so that total salt in the composition is less than about 1% or lower, a stable 1-phase product can be formulated. Whereas, if the regular material with high inorganic salt is used, the product is cloudy, 2-phase, and unstable. The cloudy 2-phase product is likely the result of a gel-like precipitate formed between the anionic surfactant and high molecular weight cationic polymer known as coacervate. The solution described herein prevents the undesired coacervate formation in product while on the shelf (before use), and yet forms coacervate when needed, during use after dilution, to deliver consumer desired wet conditioning.

The formation of coacervate upon dilution of the cleansing composition with water, rather than while in the bottle on the shelf, is important to improving wet conditioning and deposition of various conditioning actives, especially those that have small droplet sizes (i.e., <2 microns). In order to form coacervate at the right time (upon dilution during use) cleansing compositions comprising anionic surfactants substantially free of sulfates, amphoteric surfactants and cationic polymers should maintain an inorganic salt level of less than 1%.

The cleansing composition has less than 1 wt % of inorganic salt; alternatively from about 0 wt % to about 0.9 wt % of inorganic salt, alternatively from about 0 wt % to about 0.8 wt % of inorganic salt, alternatively from about 0 wt % to about 0.5 wt %, and alternatively from about 0 wt % to about 0.2 wt %.

A. Surfactant

The cleansing compositions described herein can include one or more surfactants in the surfactant system. The one or more surfactants can be substantially free of sulfate-based surfactants. As can be appreciated, surfactants provide a cleaning benefit to soiled articles such as hair, skin, and hair follicles by facilitating the removal of oil and other soils. Surfactants generally facilitate such cleaning due to their amphiphilic nature which allows for the surfactants to break up, and form micelles around, oil and other soils which can then be rinsed out, thereby removing them from the soiled article. Suitable surfactants for a cleansing composition can include anionic moieties to allow for the formation of a coacervate with a cationic polymer. The surfactant can be selected from anionic surfactants, amphoteric surfactants, zwitterionic surfactants, non-ionic surfactants, and combinations thereof.

Cleansing compositions typically employ sulfate-based surfactant systems (such as, but not limited to, sodium lauryl sulfate) because of their effectiveness in lather production, stability, clarity and cleansing. The cleansing compositions described herein are substantially free of sulfate-based surfactants. "Substantially free" of sulfate based surfactants as used herein means from about 0 wt % to about 3 wt %, alternatively from about 0 wt % to about 2 wt %, alternatively from about 0 wt % to about 1 wt %, alternatively from about 0 wt % to about 0.5 wt %, alternatively from about 0 wt % to about 0.25 wt %, alternatively from about 0 wt % to about 0.1 wt %, alternatively from about 0 wt % to about 0.05 wt %, alternatively from about 0 wt % to about 0.01 wt %, alternatively from about 0 wt % to about 0.001 wt %, and/or alternatively free of sulfates. As used herein, "free of" means 0 wt %.

Additionally, the surfactant systems described herein have from about 0 wt % to about 1 wt % of inorganic salts.

Suitable surfactants that are substantially free of sulfates can include sodium, ammonium or potassium salts of isethionates; sodium, ammonium or potassium salts of sulfonates; sodium, ammonium or potassium salts of ether sulfonates; sodium, ammonium or potassium salts of sulfosuccinates; sodium, ammonium or potassium salts of sulfoacetates; sodium, ammonium or potassium salts of glycinates; sodium, ammonium or potassium salts of sarcosinates; sodium, ammonium or potassium salts of glutamates; sodium, ammonium or potassium salts of alaninates; sodium, ammonium or potassium salts of carboxylates; sodium, ammonium or potassium salts of taurates; sodium, ammonium or potassium salts of phosphate esters; and combinations thereof.

The concentration of the surfactant in the composition should be sufficient to provide the desired cleaning and lather performance. The cleansing composition can comprise a total surfactant level of from about 6% to about 50%, from about 5% to about 35%, a total surfactant level of from about 10% to about 50%, by weight, from about 15% to about 45%, by weight, from about 20% to about 40%, by weight, from about 22% to about 35%, and/or from about 25% to about 30%.

The surfactant system can include one or more amino acid based anionic surfactants. Non-limiting examples of amino acid based anionic surfactants can include sodium, ammonium or potassium salts of acyl glycinates; sodium, ammonium or potassium salts of acyl sarcosinates; sodium, ammonium or potassium salts of acyl glutamates; sodium, ammonium or potassium salts of acyl alaninates and combinations thereof.

The amino acid based anionic surfactant can be a glutamate, for instance an acyl glutamate. The composition can comprise an acyl glutamate level from about 2% to about 22%, by weight, from about 3% to about 19%, by weight, 4% to about 17%, by weight, and/or from about 5% to about 15%, by weight.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl Glutamate, sodium olivoyl glutamate, disodium olivoyl glutamate, sodium palmoyl glutamate, disodium palmoyl Glutamate, TEA-cocoyl glutamate, TEA-hydrogenated tallowoyl glutamate, TEA-lauroyl glutamate, and mixtures thereof.

The amino acid based anionic surfactant can be an alaninate, for instance an acyl alaninate. Non-limiting example of acyl alaninates can include sodium cocoyl alaninate, sodium lauroyl alaninate, sodium N-dodecanoyl-1-alaninate and combination thereof. The composition can comprise an acyl alaninate level from about 2% to about 20%, by weight, from about 7% to about 15%, by weight, and/or from about 8% to about 12%, by weight.

The amino acid based anionic surfactant can be a sarcosinate, for instance an acyl sarcosinate. Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroylglutamate/lauroylsarcosinate, disodium lauroamphodiacetate lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

The amino acid based anionic surfactant can be a glycinate for instance an acyl glycinate. Non-limiting example of acyl glycinates can include sodium cocoyl glycinate, sodium lauroyl glycinate and combination thereof.

The composition can contain additional anionic surfactants selected from the group consisting of sulfosuccinates, isethionates, sulfonates, sulfoacetates, glucose carboxylates, alkyl ether carboxylates, acyl taurates, and mixture thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof. The composition can comprise a sulfosuccinate level from about 2% to about 22%, by weight, from about 3% to about 19%, by weight, 4% to about 17%, by weight, and/or from about 5% to about 15%, by weight.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sulfonates can include alpha olefin sulfonates, linear alkylbenzene sulfonates, sodium laurylglucosides hydroxypropylsulfonate and combination thereof.

Non-limiting examples of sulfoacetates can include sodium lauryl sulfoacetate, ammonium lauryl sulfoacetate and combination thereof.

Non-limiting example of glucose carboxylates can include sodium lauryl glucoside carboxylate, sodium cocoyl glucoside carboxylate and combinations thereof.

Non-limiting example of alkyl ether carboxylate can include sodium laureth-4 carboxylate, laureth-5 carboxylate, laureth-13 carboxylate, sodium C12-13 pareth-8 carboxylate, sodium C12-15 pareth-8 carboxylate and combination thereof.

Non-limiting example of acyl taurates can include sodium methyl cocoyl taurate, sodium methyl lauroyl taurate, sodium methyl oleoyl taurate and combination thereof.

The surfactant system may further comprise one or more amphoteric surfactants and the amphoteric surfactant can be selected from the group consisting of betaines, sultaines, hydroxysultanes, amphohydroxypropyl sulfonates, alkyl amphoactates, alkyl amphodiacetates and combination thereof.

Examples of betaine amphoteric surfactants can include coco dimethyl carboxymethyl betaine, cocoamidopropyl betaine (CAPB), cocobetaine, lauryl amidopropyl betaine (LAPB), oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines can include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

Non-limiting example of alkylamphoacetates can include sodium cocoyl amphoacetate, sodium lauroyl amphoacetate and combination thereof.

The amphoteric surfactant can comprise cocamidopropyl betaine (CAPB), lauramidopropyl betaine (LAPB), and combinations thereof.

The cleansing composition can comprise a amphoteric surfactant level from about 0.5 wt % to about 20 wt %, from about 1 wt % to about 15 wt %, from about 2 wt % to about 13 wt %, from about 3 wt % to about 15 wt %, and/or from about 5 wt % to about 10 wt %.

The surfactant system can have a weight ratio of anionic surfactant to amphoteric surfactant from about 1:5 to about 10:1, from about 1:2 to about 7:1, from 1:1 to about 5:1, and/or from about 2:1 to about 4:1. The surfactant system can have a weight ratio of anionic surfactant to amphoteric surfactant greater than 1:1, greater than 3:2, greater than 9:5, and/or greater than 2:1.

The surfactant system may further comprise one or more non-ionic surfactants and the non-ionic surfactant can be selected from the group consisting alkyl polyglucoside, alkyl glycoside, acyl glucamide and mixture thereof. Non-limiting examples of alkyl glucosides can include decyl glucoside, cocoyl glucoside, lauroyl glucoside and combination thereof.

Non-limiting examples of acyl glucamide can include lauroyl/myristoyl methyl glucamide, capryloyl/caproyl methyl glucamide, lauroyl/myristoyl methyl glucamide, cocoyl methyl glucamide and combinations thereof.

B. Cationic Polymer

A cleansing composition can include a cationic polymer to allow formation of a coacervate. As can be appreciated, the cationic charge of a cationic polymer can interact with an anionic charge of a surfactant to form the coacervate. Suitable cationic polymers can include: (a) a cationic guar polymer, (b) a cationic non-guar galactomannan polymer, (c) a cationic starch polymer, (d) a cationic copolymer of acrylamide monomers and cationic monomers, (e) a synthetic, non-crosslinked, cationic polymer, which may or may not form lyotropic liquid crystals upon combination with the detersive surfactant, and (f) a cationic cellulose polymer. In certain examples, more than one cationic polymer can be included.

A cationic polymer can be included by weight of the cleansing composition at about 0.05% to about 3%, about 0.075% to about 2.0%, or at about 0.1% to about 1.0%. Cationic polymers can have cationic charge densities of about 0.9 meq/g or more, about 1.2 meq/g or more, and about 1.5 meq/g or more. However, cationic charge density can also be about 7 meq/g or less and alternatively about 5 meq/g or less. The charge densities can be measured at the pH of intended use of the cleansing composition. (e.g., at about pH 3 to about pH 9; or about pH 4 to about pH 8). The average molecular weight of cationic polymers can generally be between about 10,000 and 10 million, between about 50,000 and about 5 million, and between about 100,000 and about 3 million, and between about 300,000 and about 3 million and between about 100,000 and about 2.5 million. Low molecular weight cationic polymers can be used. Low molecular weight cationic polymers can have greater translucency in the liquid carrier of a cleansing composition. The cationic polymer can be a single type, such as the cationic guar polymer guar hydroxypropyltrimonium chloride having a weight average molecular weight of about 2.5 million g/mol or less, and the cleansing composition can have an additional cationic polymer of the same or different types.

Cationic Guar Polymer

The cationic polymer can be a cationic guar polymer, which is a cationically substituted galactomannan (guar) gum derivative. Suitable guar gums for guar gum derivatives can be obtained as a naturally occurring material from the seeds of the guar plant. As can be appreciated, the guar molecule is a straight chain mannan which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums can be obtained through reactions between the hydroxyl groups of the polygalactomannan and reactive quaternary ammonium compounds. The degree of substitution of the cationic groups onto the guar structure can be sufficient to provide the requisite cationic charge density described above.

A cationic guar polymer can have a weight average molecular weight ("M.Wt.") of less than about 3 million g/mol, and can have a charge density from about 0.05 meq/g to about 2.5 meq/g. Alternatively, the cationic guar polymer can have a weight average M.Wt. of less than 1.5 million g/mol, from about 150 thousand g/mol to about 1.5 million g/mol, from about 200 thousand g/mol to about 1.5 million g/mol, from about 300 thousand g/mol to about 1.5 million g/mol, and from about 700,000 thousand g/mol to about 1.5 million g/mol. The cationic guar polymer can have a charge density from about 0.2 meq/g to about 2.2 meq/g, from about 0.3 meq/g to about 2.0 meq/g, from about 0.4 meq/g to about 1.8 meq/g; and from about 0.5 meq/g to about 1.7 meq/g.

A cationic guar polymer can have a weight average M.Wt. of less than about 1 million g/mol, and can have a charge density from about 0.1 meq/g to about 2.5 meq/g. A cationic guar polymer can have a weight average M.Wt. of less than 900 thousand g/mol, from about 150 thousand to about 800 thousand g/mol, from about 200 thousand g/mol to about 700 thousand g/mol, from about 300 thousand to about 700 thousand g/mol, from about 400 thousand to about 600 thousand g/mol, from about 150 thousand g/mol to about 800 thousand g/mol, from about 200 thousand g/mol to about 700 thousand g/mol, from about 300 thousand g/mol to about 700 thousand g/mol, and from about 400 thousand g/mol to about 600 thousand g/mol. A cationic guar polymer has a charge density from about 0.2 meq/g to about 2.2 meq/g, from about 0.3 meq/g to about 2.0 meq/g, from about 0.4 meq/g to about 1.8 meq/g; and from about 0.5 meq/g to about 1.5 meq/g.

A cleansing composition can include from about 0.01% to less than about 0.7%, by weight of the cleansing composition of a cationic guar polymer, from about 0.04% to about 0.55%, by weight, from about 0.08% to about 0.5%, by weight, from about 0.16% to about 0.5%, by weight, from about 0.2% to about 0.5%, by weight, from about 0.3% to about 0.5%, by weight, and from about 0.4% to about 0.5%, by weight.

The cationic guar polymer can be formed from quaternary ammonium compounds which conform to general Formula II:

Formula II

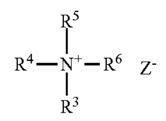

wherein where $R^3$, $R^4$ and $R^5$ are methyl or ethyl groups; and $R^6$ is either an epoxyalkyl group of the general Formula III:

Formula III

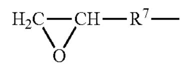

or $R^6$ is a halohydrin group of the general Formula IV:

Formula IV

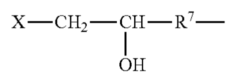

wherein $R^7$ is a $C_1$ to $C_3$ alkylene; X is chlorine or bromine, and Z is an anion such as Cl—, Br—, I— or $HSO_4$—.

Suitable cationic guar polymers can conform to the general formula V:

Formula V

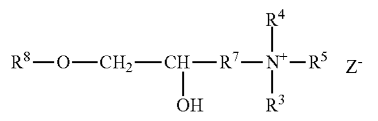

wherein $R^8$ is guar gum; and wherein $R^4$, $R^5$, $R^6$ and $R^7$ are as defined above; and wherein Z is a halogen. Suitable cationic guar polymers can conform to Formula VI:

Formula VI

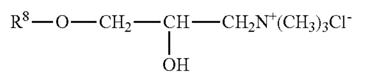

wherein $R^8$ is guar gum.

Suitable cationic guar polymers can also include cationic guar gum derivatives, such as guar hydroxypropyltrimonium chloride. Suitable examples of guar hydroxypropyltrimonium chlorides can include the Jaguar® series commercially available from Solvay S. A., Hi-Care Series from Rhodia, and N-Hance and AquaCat from Ashland Inc. Jaguar® C-500 has a charge density of 0.8 meq/g and a M.Wt. of 500,000 g/mole; Jaguar Optima has a cationic charge density of about 1.25 meg/g and a M.Wt. of about 500,000 g/moles; Jaguar® C-17 has a cationic charge density of about 0.6 meq/g and a M.Wt. of about 2.2 million g/mol; Jaguar® and a cationic charge density of about 0.8 meq/g; Hi-Care 1000 has a charge density of about 0.7 meq/g and a M.Wt. of about 600,000 g/mole; N-Hance 3269 and N-Hance 3270, have a charge density of about 0.7 meq/g and a M.Wt. of about 425,000 g/mole; N-Hance 3196 has a charge density of about 0.8 meq/g and a M.Wt. of about 1,100,000 g/mole; and AquaCat CG518 has a charge density of about 0.9 meq/g and a M.Wt. of about 50,000 g/mole. N-Hance BF-13 and N-Hance BF-17 are borate (boron) free guar polymers. N-Hance BF-13 has a charge density of about 1.1 meq/g and M.W.t of about 800,000 and N-Hance BF-17 has a charge density of about 1.7 meq/g and M.W.t of about 800,000. BF-17 has a charge density of about 1.7 meq/g and M.W.t of about 800,000. BF-17 has a charge density of about 1.7 meq/g and M.W.t of about 800,000. BF-17 has a charge density of about 1.7 meq/g and M.W.t of about 800,000. BF-17 has a charge density of about 1.7 meq/g and M.W.t of about 800,000.

Cationic Non-Guar Galactomannan Polymer

The cationic polymer can be a galactomannan polymer derivative. Suitable galactomannan polymer can have a mannose to galactose ratio of greater than 2:1 on a monomer to monomer basis and can be a cationic galactomannan polymer derivative or an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers can be present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and can be affected by climate. Non Guar Galactomannan polymer derivatives can have a ratio of mannose to galactose of greater than 2:1 on a monomer to monomer basis. Suitable ratios of mannose to galactose can also be greater than 3:1 or greater than 4:1. Analysis of mannose to galactose ratios is well known in the art and is typically based on the measurement of the galactose content.

The gum for use in preparing the non-guar galactomannan polymer derivatives can be obtained from naturally occurring materials such as seeds or beans from plants. Examples of various non-guar galactomannan polymers include Tara gum (3 parts mannose/1 part galactose), Locust bean or Carob (4 parts mannose/1 part galactose), and *Cassia* gum (5 parts mannose/1 part galactose).

A non-guar galactomannan polymer derivative can have a M. Wt. from about 1,000 g/mol to about 10,000,000 g/mol, and a M.Wt. from about 5,000 g/mol to about 3,000,000 g/mol.

The cleansing compositions described herein can include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure can be sufficient to provide the requisite cationic charge density.

A galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general Formulas II to VI, as defined above.

Cationic non-guar galactomannan polymer derivatives formed from the reagents described above can be represented by the general Formula VII:

Formula VII

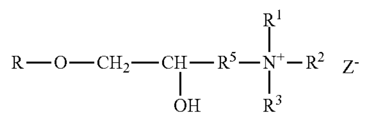

wherein R is the gum. The cationic galactomannan derivative can be a gum hydroxypropyltrimethylammonium chloride, which can be more specifically represented by the general Formula VIII:

Formula VIII

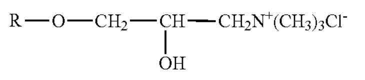

The galactomannan polymer derivative can be an amphoteric galactomannan polymer derivative having a net positive charge, obtained when the cationic galactomannan polymer derivative further comprises an anionic group.

A cationic non-guar galactomannan can have a ratio of mannose to galactose which is greater than about 4:1, a M.Wt. of about 100,000 g/mol to about 500,000 g/mol, a M.Wt. of about 50,000 g/mol to about 400,000 g/mol, and a cationic charge density from about 1 meq/g to about 5 meq/g, and from about 2 meq/g to about 4 meq/g.

Cleansing compositions can include at least about 0.05% of a galactomannan polymer derivative by weight of the composition. The cleansing compositions can include from about 0.05% to about 2%, by weight of the composition, of a galactomannan polymer derivative.

Cationic Starch Polymers

Suitable cationic polymers can also be water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The cleansing compositions described herein can include cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers can have a molecular weight from about 850,000 g/mol to about 15,000,000 g/mol and from about 900,000 g/mol to about 5,000,000 g/mol.

Cationically modified starch polymers can have a charge density of from about 0.2 meq/g to about 5 meq/g, and from about 0.2 meq/g to about 2 meq/g. The chemical modification to obtain such a charge density can include the addition of amino and/or ammonium groups into the starch molecules. Non-limiting examples of such ammonium groups can include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. Further details are described in Solarek, D. B., Cationic Starches in Modified Starches: Properties and Uses, Wurzburg, O. B., Ed., CRC Press, Inc., Boca Raton, Fla. 1986, pp 113-125 which is hereby incorporated by reference. The cationic groups can be added to the starch prior to degradation to a smaller molecular weight or the cationic groups may be added after such modification.

A cationically modified starch polymer can have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution can be determined using proton nuclear magnetic resonance spectroscopy ("$^1$H NMR") methods well known in the art. Suitable $^1$H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be selected from a variety of sources such as tubers, legumes, cereal, and grains. For example, starch sources can include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof. Suitable cationically modified starch polymers can be selected from degraded cationic maize starch, cationic tapioca, cationic potato starch, and mixtures thereof. Cationically modified starch polymers are cationic corn starch and cationic tapioca.

The starch, prior to degradation or after modification to a smaller molecular weight, can include one or more additional modifications. For example, these modifications may include cross-linking, stabilization reactions, phosphorylations, and hydrolyzations. Stabilization reactions can include alkylation and esterification.

Cationically modified starch polymers can be included in a cleansing composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

The starch can be readily soluble in water and can form a substantially translucent solution in water. The transparency of the composition is measured by Ultra-Violet/Visible ("UV/VIS") spectrophotometry, which determines the absorption or transmission of UV/VIS light by a sample, using a Gretag Macbeth Colorimeter Color. A light wavelength of 600 nm has been shown to be adequate for characterizing the degree of clarity of cleansing compositions.

Cationic Copolymer of an Acrylamide Monomer and a Cationic Monomer

A cleansing composition can include a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

Suitable cationic polymers can include:

(i) an acrylamide monomer of the following Formula IX:

Formula IX

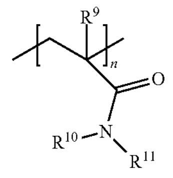

where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula X:

Formula X

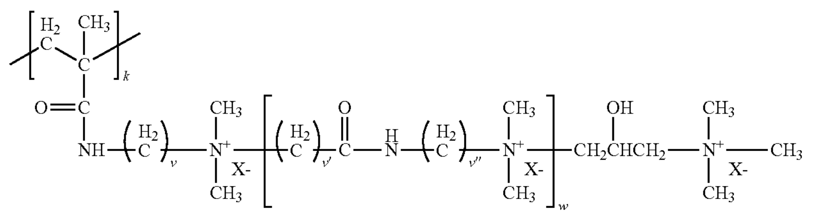

where k=1, each of v, v', and v" is independently an integer of from 1 to 6, w is zero or an integer of from 1 to 10, and $X^-$ is an anion.

A cationic monomer can conform to Formula X where k=1, v=3 and w=0, z=1 and $X^-$ is $Cl^-$ to form the following structure (Formula XI):

Formula XI

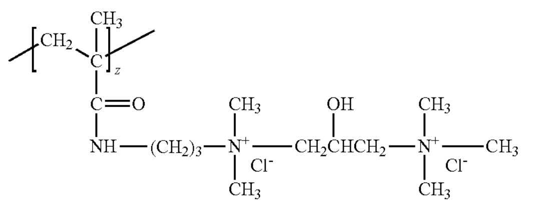

As can be appreciated, the above structure can be referred to as diquat.

A cationic monomer can conform to Formula X wherein v and v" are each 3, V'=1, w=1, y=1 and $X^-$ is $Cl^-$ to form the following structure of Formula XII:

Formula XII

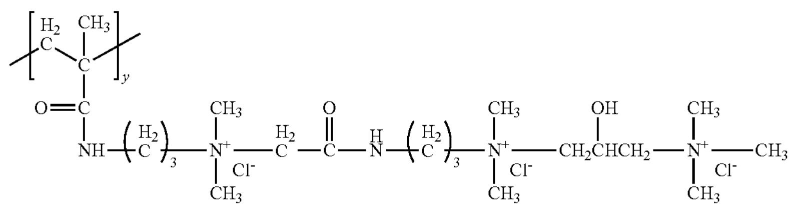

The structure of Formula XII can be referred to as triquat.

The acrylamide monomer can be either acrylamide or methacrylamide.

The cationic copolymer can be AM:TRIQUAT which is a copolymer of acrylamide and 1,3-Propanediaminium,N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT can have a charge density of 1.6 meq/g and a M.Wt. of 1.1 million g/mol.

The cationic copolymer can include an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can include a cationic monomer selected from the group consisting of: trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters can be cationized esters of the (meth)acrylic acid containing a quaternized N atom. Cationized esters of the (meth)acrylic acid containing a quaternized N atom can be quaternized dialkylaminoalkyl (meth)acrylates with C1 to $C_3$ in the alkyl and alkylene groups. The cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth) acrylate; and diethylaminopropyl (meth)acrylate quaternized with methyl chloride. The cationized esters of the (meth)acrylic acid containing a quaternized N atom can be dimethylaminoethyl acrylate, which is quaternized with an alkyl halide, or with methyl chloride or benzyl chloride or dimethyl sulfate (ADAME-Quat). The cationic monomer when based on (meth)acrylamides are quaternized dialkylaminoalkyl(meth)acrylamides with $C_1$ to $C_3$ in the alkyl and alkylene groups, or dimethylaminopropylacrylamide, which is quaternized with an alkyl halide, or methyl chloride or benzyl chloride or dimethyl sulfate.

The cationic monomer based on a (meth)acrylamide can be a quaternized dialkylaminoalkyl(meth)acrylamide with $C_1$ to $C_3$ in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, any monomer that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, from about 1.1 meq/g to about 2.3 meq/g, from about 1.2 meq/g to about 2.2 meq/g, from about 1.2 meq/g to about 2.1 meq/g, from about 1.3 meq/g to about 2.0 meq/g, and from about 1.3 meq/g to about 1.9 meq/g.

The cationic copolymer can have a M.Wt. from about 100 thousand g/mol to about 2 million g/mol, from about 300 thousand g/mol to about 1.8 million g/mol, from about 500 thousand g/mol to about 1.6 million g/mol, from about 700 thousand g/mol to about 1.4 million g/mol, and from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC can have a charge density of about 1.3 meq/g and a M.Wt. of about 1.1 million g/mol. The cationic copolymer can be AM:ATPAC. AM:ATPAC can have a charge density of about 1.8 meq/g and a M.Wt. of about 1.1 million g/mol.

Synthetic Polymers

A cationic polymer can be a synthetic polymer that is formed from:

i) one or more cationic monomer units, and optionally
ii) one or more monomer units bearing a negative charge, and/or
iii) a nonionic monomer,
  wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers which have the structure of Formula XIII:

Formula XIII

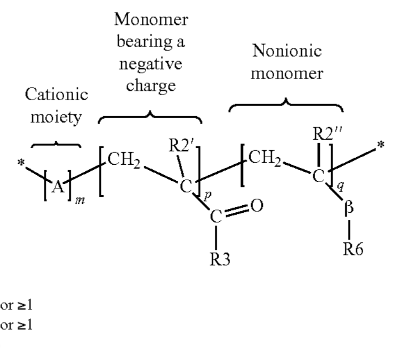

m ≥ 1
p = 0 or ≥1
q = 0 or ≥1
m ≥ p where A, may be one or more of the following cationic moieties:

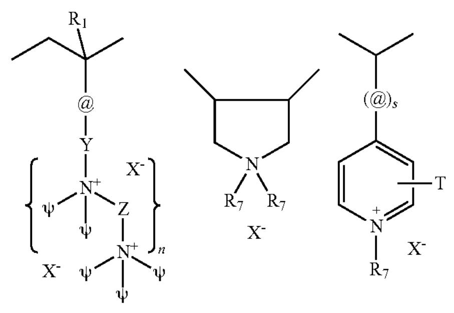

where @=amido, alkylamido, ester, ether, alkyl or alkylaryl;

where Y=C1-C22 alkyl, alkoxy, alkylidene, alkyl or aryloxy;

where ψ=C1-C22 alkyl, alkyloxy, alkyl aryl or alkyl arylox;

where Z=C1-C22 alkyl, alkyloxy, aryl or aryloxy;

where R1=H, C1-C4 linear or branched alkyl;

where s=0 or 1,n=0 or ≥1;

where T and R7=C1-C22 alkyl; and where X−=halogen, hydroxide, alkoxide, sulfate or alkylsulfate.

Where the monomer bearing a negative charge is defined by R2'=H, $C_1$-$C_4$ linear or branched alkyl and R3 is:

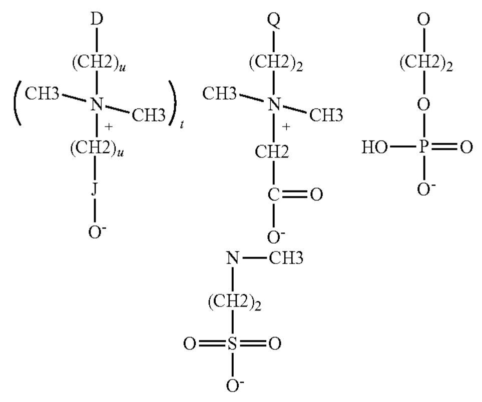

where D=O, N, or S;

where Q=$NH_2$ or 0;

where u=1-6;

where t=0-1; and where J=oxygenated functional group containing the following elements P, S, C.

Where the nonionic monomer is defined by R2"=H, $C_1$-$C_4$ linear or branched alkyl, R6=linear or branched alkyl, alkyl aryl, aryl oxy, alkyloxy, alkylaryl oxy and β is defined as

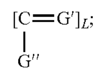

where G' and G" are, independently of one another, O, S or N—H and L=0 or 1.

Suitable monomers can include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of suitable cationic monomers can include dimethylaminoethyl (meth)acrylate, dimethylaminopropyl (meth)acrylate, ditertiobutylaminoethyl (meth) acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers can include quaternary monomers of formula —$NR_3$+, wherein each R can be identical or different, and can be a hydrogen atom, an alkyl group comprising 1 to 10 carbon atoms, or a benzyl group, optionally carrying a hydroxyl group, and including an anion (counter-ion). Examples of suitable anions include halides such as chlorides, bromides, sulphates, hydrosulphates, alkylsulphates (for example comprising 1 to 6 carbon atoms), phosphates, citrates, formates, and acetates.

Suitable cationic monomers can also include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride. Additional suitable cationic monomers can include trimethyl ammonium propyl (meth) acrylamido chloride.

Examples of monomers bearing a negative charge include alpha ethylenically unsaturated monomers including a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge can include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers can include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers can also include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X−) in association with the synthetic cationic polymers can be any known counterion so long as the polymers remain soluble or dispersible in water, in the cleansing composition, or in a coacervate phase of the cleansing composition, and so long as the counterions are physically and chemically compatible with the essential components of the cleansing composition or do not otherwise unduly impair product performance, stability or aesthetics. Non limiting examples of suitable counterions can include halides (e.g., chlorine, fluorine, bromine, iodine), sulfate, and methylsulfate.

The cationic polymer described herein can also aid in repairing damaged hair, particularly chemically treated hair by providing a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer can return the hair to a generally virgin-like, healthier state. Lyotropic liquid crystals are formed by combining the synthetic cationic polymers described herein with the aforementioned anionic detersive surfactant component of the cleansing composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in PCT Patent App. No. WO 94/06403 which is incorporated by reference. The synthetic polymers described herein can be formulated in a stable cleansing composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. The cationic charge density is about 6.2 meq/gm. The polymers also have a M. Wt. of from about 1,000 to about 5,000,000, and/or from about 10,000 to about 2,000,000, and/or from about 100,000 to about 2,000,000.

Cationic synthetic polymers that provide enhanced conditioning and deposition of benefit agents but do not necessarily form lytropic liquid crystals can have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M.Wt. of from about 1,000 g/mol to about 5,000,000 g/mol, from about 10,000 g/mol to about 2,000,000 g/mol, and from about 100,000 g/mol to about 2,000,000 g/mol.

Cationic Cellulose Polymer

Suitable cationic polymers can be cellulose polymers. Suitable cellulose polymers can include salts of hydroxyethyl cellulose reacted with trimethyl ammonium substituted epoxide, referred to in the industry (CTFA) as Polyquaternium 10 and available from Dwo/Amerchol Corp. (Edison, N.J., USA) in their Polymer LR, JR, and KG series of polymers. Other suitable types of cationic cellulose can include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose can include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Additional cationic polymers are also described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which is incorporated herein by reference.

Techniques for analysis of formation of complex coacervates are known in the art. For example, microscopic analyses of the compositions, at any chosen stage of dilution, can be utilized to identify whether a coacervate phase has formed. Such coacervate phase can be identifiable as an additional emulsified phase in the composition. The use of dyes can aid in distinguishing the coacervate phase from other insoluble phases dispersed in the composition. Additional details about the use of cationic polymers and coacervates are disclosed in U.S. Pat. No. 9,272,164 which is incorporated by reference.

C. Liquid Carrier

As can be appreciated, cleansing compositions can desirably be in the form of pourable liquid under ambient conditions. Inclusion of an appropriate quantity of a liquid carrier can facilitate the formation of a cleansing composition having an appropriate viscosity and rheology. A cleansing composition can include, by weight of the composition, about 20% to about 95%, by weight, of a liquid carrier, and about 60% to about 85%, by weight, of a liquid carrier. The liquid carrier can be an aqueous carrier such as water.

D. Optional Components

As can be appreciated, cleansing compositions described herein can include a variety of optional components to tailor the properties and characteristics of the composition. As can be appreciated, suitable optional components are well known and can generally include any components which are physically and chemically compatible with the essential components of the cleansing compositions described herein. Optional components should not otherwise unduly impair product stability, aesthetics, or performance. Individual concentrations of optional components can generally range from about 0.001% to about 10%, by weight of a cleansing composition. Optional components can be further limited to components which will not impair the clarity of a translucent cleansing composition.

Suitable optional components which can be included in a cleansing composition can include co-surfactants, deposition aids, conditioning agents (including hydrocarbon oils, fatty esters, silicones), anti-dandruff agents, suspending agents, viscosity modifiers, dyes, nonvolatile solvents or diluents (water soluble and insoluble), pearlescent aids, foam boosters, pediculocides, pH adjusting agents, perfumes, preservatives, chelants, proteins, skin active agents, sunscreens, UV absorbers, and vitamins. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to the composition herein.

Conditioning Agents

A cleansing composition can include a silicone conditioning agent. Suitable silicone conditioning agents can include volatile silicone, non-volatile silicone, or combinations thereof. If including a silicone conditioning agent, the agent can be included from about 0.01% to about 10%, by weight of the composition, from about 0.1% to about 8%, from about 0.1% to about 5%, and/or from about 0.2% to about 3%. Examples of suitable silicone conditioning agents, and optional suspending agents for the silicone, are described in U.S. Reissue Pat. No. 34,584, U.S. Pat. Nos. 5,104,646, and 5,106,609, each of which is incorporated by reference herein. Suitable silicone conditioning agents can have a viscosity, as measured at 25° C., from about 20 centistokes ("csk") to about 2,000,000 csk, from about 1,000 csk to about 1,800,000 csk, from about 50,000 csk to about 1,500,000 csk, and from about 100,000 csk to about 1,500,000 csk.

The dispersed silicone conditioning agent particles can have a volume average particle diameter ranging from about 0.01 micrometer to about 50 micrometer. For small particle application to hair, the volume average particle diameters can range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), which is incorporated herein by reference.

Silicone emulsions suitable for the cleansing compositions described herein can include emulsions of insoluble polysiloxanes prepared in accordance with the descriptions provided in U.S. Pat. No. 4,476,282 and U.S. Patent Application Publication No. 2007/0276087 each of which is incorporated herein by reference. Suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

Other classes of silicones suitable for the cleansing compositions described herein can include i) silicone fluids, including silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Alternatively, the cleansing composition can be substantially free of silicones. As used herein, substantially free of silicones means from about 0 to about 0.2 wt. %.

Organic Conditioning Materials

The conditioning agent of the cleansing compositions described herein can also include at least one organic conditioning material such as oil or wax, either alone or in combination with other conditioning agents, such as the silicones described above. The organic material can be non-polymeric, oligomeric or polymeric. The organic material can be in the form of an oil or wax and can be added in the cleansing formulation neat or in a pre-emulsified form. Suitable examples of organic conditioning materials can include: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Emulsifiers

A variety of anionic and nonionic emulsifiers can be used in the cleansing composition of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

Chelating Agents

The cleansing composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440. U.S. Pat. Nos. 5,284,972 and 5,747,440 are each incorporated by reference herein. Suitable chelants can further include histidine.

Levels of an EDDS chelant or histidine chelant in the cleansing compositions can be low. For example, an EDDS chelant or histidine chelant can be included at about 0.01%, by weight. Above about 10% by weight, formulation and/or human safety concerns can arise. The level of an EDDS chelant or histidine chelant can be at least about 0.01%, by weight, at least about 0.05%, by weight, at least about 0.1%, by weight, at least about 0.25%, by weight, at least about 0.5%, by weight, at least about 1%, by weight, or at least about 2%, by weight, by weight of the cleansing composition.

Gel Network

A cleansing composition can also include a fatty alcohol gel network. Gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. Gel networks can provide a number of benefits to cleansing compositions. For example, a gel network can provide a stabilizing benefit to cosmetic creams and hair conditioners. In addition, gel networks can provide conditioned feel benefits to hair conditioners and shampoos.

A fatty alcohol can be included in the gel network at a level by weight of from about 0.05%, by weight, to about 14%, by weight. For example, the fatty alcohol can be included in an amount ranging from about 1%, by weight, to about 10%, by weight, and/or from about 6%, by weight, to about 8%, by weight.

Suitable fatty alcohols include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Nonlimiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

A gel network can be prepared by charging a vessel with water. The water can then be heated to about 74° C. Cetyl alcohol, stearyl alcohol, and surfactant can then be added to the heated water. After incorporation, the resulting mixture can passed through a heat exchanger where the mixture is cooled to about 35° C. Upon cooling, the fatty alcohols and surfactant crystallized can form crystalline gel network. Table 1 provides the components and their respective amounts for an example gel network composition.

To prepare the gel network pre-mix of Table 1, water is heated to about 74° C. and the fatty alcohol and gel network surfactant are added to it in the quantities depicted in Table 1. After incorporation, this mixture is passed through a mill and heat exchanger where it is cooled to about 32° C. As a result of this cooling step, the fatty alcohol, the gel network surfactant, and the water form a crystalline gel network.

TABLE 1

| Premix | % |
|---|---|
| Gel Network Surfactant[1] | 11.00 |
| Stearyl Alcohol | 8% |
| Cetyl Alcohol | 4% |
| Water | QS |

[1]For anionic gel networks, suitable gel network surfactants above include surfactants with a net negative charge including sulfonates, carboxylates, and phosphates among others and mixtures thereof.

For cationic gel networks, suitable gel network surfactants above include surfactants with a net positive charge including quaternary ammonium surfactants and mixtures thereof. For Amphoteric or Zwitterionic gel networks, suitable gel network surfactants above include surfactants with both a positive and negative charge at product usage pH including betaines, amine oxides, sultaines, amino acids among others and mixtures thereof.

Benefit Agents

A cleansing composition can further include one or more benefit agents. Exemplary benefit agents include, but are not limited to, particles, colorants, perfume microcapsules, gel networks, and other insoluble skin or hair conditioning agents such as skin silicones, natural oils such as sun flower oil or castor oil. The benefit agent can be selected from the group consisting of: particles; colorants; perfume microcapsules; gel networks; other insoluble skin or hair conditioning agents such as skin silicones, natural oils such as sun flower oil or castor oil; and mixtures thereof.

Suspending Agent

A cleansing composition can include a suspending agent at concentrations effective for suspending water-insoluble material in dispersed form in the compositions or for modifying the viscosity of the composition. Such concentrations range from about 0.05% to about 10%, and from about 0.3% to about 5.0%, by weight of the compositions. As can be appreciated however, suspending agents may not be necessary when certain glyceride ester crystals are included as certain glyceride ester crystals can act as suitable suspending or structuring agents.

Suitable suspending agents can include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Other suitable suspending agents can include crystalline suspending agents which can be categorized as acyl derivatives, long chain amine oxides, and mixtures thereof. Examples of such suspending agents are described in U.S. Pat. No. 4,741,855, which is incorporated herein by reference. Suitable suspending agents include ethylene glycol esters of fatty acids having from 16 to 22 carbon atoms. The suspending agent can be an ethylene glycol stearates, both mono and distearate, but particularly the distearate containing less than about 7% of the mono stearate. Other suitable suspending agents include alkanol amides of fatty acids, having from about 16 to about 22 carbon atoms, alternatively from about 16 to about 18 carbon atoms, suitable examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters as previously described. Long chain acyl derivatives, ethylene glycol esters of long chain carboxylic acids, long chain amine oxides, and alkanol amides of long chain carboxylic acids can also be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents include crystallizable glyceride esters. For example, in certain embodiments, suitable glyceride esters are hydrogenated castor oils such as trihydroxystearin or dihydroxystearin. Examples of additional crystallizable glyceride esters can include the substantially pure triglyceride of 12-hydroxystearic acid. 12-hydroxystearic acid is the pure form of a fully hydrogenated triglyceride of 12-hydrox-9-cis-octadecenoic acid. As can be appreciated, many additional glyceride esters are possible. For example, variations in the hydrogenation process and natural variations in castor oil can enable the production of additional suitable glyceride esters from castor oil.

Viscosity Modifiers

Viscosity modifiers can be used to modify the rheology of a cleansing composition. Suitable viscosity modifiers can include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol. Sodium chloride can also be used as a viscosity modifier. Other suitable rheology modifiers can include cross-linked acrylates, cross-linked maleic anhydride co-methylvinylethers, hydrophobically modified associative polymers, and mixtures thereof.

The cleansing composition can have a viscosity of about 1 cP to about 20,000 cP, or from about 100 cps to about 15,000 cps, or from 2,500 cP to about 12,000 cP, or from 1 cP to about 5000 cP, or from about 3,500 cP to about 8,500 cP, measured at 26.6° C. with a Brookfield R/S Plus Rheometer at 2 $s^{-1}$. cP means centipoises.

Dispersed Particles

Dispersed particles as known in the art can be included in a cleansing composition. If including such dispersed particles, the particles can be incorporated, by weight of the composition, at levels of about 0.025% or more, about 0.05% or more, about 0.1% or more, about 0.25% or more, and about 0.5% or more. However, the cleansing compositions can also contain, by weight of the composition, about 20% or fewer dispersed particles, about 10% or fewer dispersed particles, about 5% or fewer dispersed particles, about 3% or fewer dispersed particles, and about 2% or fewer dispersed particles.

As can be appreciated, a cleansing composition can include still further optional components. For example, amino acids can be included. Suitable amino acids can include water soluble vitamins such as vitamins B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

Anti-dandruff agents can be included. As can be appreciated, the formation of a coacervate can facilitate deposition of the anti-dandruff agent to the scalp.

A cleansing composition can optionally include pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions can also include antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

One or more stabilizers can be included. For example, one or more of ethylene glycol distearate, citric, citrate, a preservative such as kathon, sodium benzoate, sodium salicylate and ethylenediaminetetraacetic acid ("EDTA") can be included to improve the lifespan of a cleansing composition.

Foam Dispenser

The shampoo composition can be stored and dispensed from an aerosol foam dispenser that can include a reservoir for holding the shampoo composition. The reservoir may be made from any suitable material including materials selected from the group consisting of plastic, metal, alloy, laminate, and combinations thereof. The reservoir may be for one-time use. The reservoir may be removable from the aerosol foam dispenser. Alternatively, the reservoir may be integrated with the aerosol foam dispenser. Alternatively, there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

Alternatively, the hair composition can be stored and dispensed from a mechanical foam dispenser. Non-limiting examples of suitable pump dispensers include those described in WO 2004/078903, WO 2004/078901, and WO 2005/078063 and may be supplied by Albea (60 Electric Ave., Thomaston, CT 06787 USA) or Rieke Packaging Systems (500 West Seventh St., Auburn, Indiana 46706).

The shampoo composition can be stored and dispensed from a squeeze foam dispenser. An example of squeeze foamer is EZ'R available from Albéa.

The shampoo composition and/or the dispenser can be free or substantially free of a propellant, for instance aerosol propellants.

Propellant

The shampoo composition described herein may comprise from about from about 2% to about 10% propellant, alternatively from about 3% to about 8% propellant, and alternatively from about 4% to about 7% propellant, by weight of the shampoo.

The propellant may comprise one or more volatile materials, which in a gaseous state, may carry the other components of the shampoo in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the shampoo composition.

Aerosol propellants which may be employed in the aerosol composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene (HFO 1234ze available by Honeywell), and mixtures thereof. The propellant may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar. The propellant may comprise hydrofluoroolefins (HFOs).

Compositions that use an HFO propellant can have a higher foam densities (approximately 2× greater) versus hydrocarbon propellants and at equal formula pressure and formula % saturated pressure. The higher density can enable higher gravimetric foam dosage per unit volume of the resulting dispensed foam shampoo. This means that a consumer could use a smaller volume of foam to achieve similar results when using a less dense foam.

The pressure and % saturated pressure can be important to enable sufficient foam dispensing over the life of the product (from beginning to middle to end of the pressurized container). The 1,3,3,3-tetrafluoropropene can also enable significantly greater gloss or shine of the dispensed foam.

Method of Making a Cleansing Composition

A cleansing composition described herein can be formed similarly to known cleansing compositions. For example, the process of making a cleansing composition can include the step of mixing the surfactant, cationic polymer, and liquid carrier together to form a cleansing composition.

Test Methods

A. Clarity Assessment

Measurement of % Transmittance (% T)

Techniques for analysis of formation of complex coacervates are known in the art. One method to assess coacervate formation upon dilution for a transparent or translucent composition is to use a spectrophotometer to measure the percentage of light transmitted through the diluted sample (% T). As percent light transmittance (% T) values measured of the dilution decrease, typically higher levels of coacervate are formed. Dilutions samples at various weight ratios of water to composition can be prepared, for example 2 parts of water to 1 part composition (2:1), or 7.5 parts of water to 1 part composition (7.5:1), or 16 parts of water to 1 part composition (16:1), or 34 parts of water to 1 part composition (34:1), and the % T measured for each dilution ratio sample. Examples of possible dilution ratios may include 2:1, 3:1, 5:1, 7.5:1, 11:1, 16:1, 24:1, or 34:1. By averaging the % T values for samples that span a range of dilution ratios, it is possible to simulate and ascertain how much coacervate a composition on average would form as a consumer applies the composition to wet hair, lathers, and then rinses it out. Average % T can be calculated by taking the numerical average of individual % T measurements for the following dilution ratios: 2:1, 3:1, 5:1, 7.5:1, 11:1, 16:1,24:1, and 34:1.

% T can be measured using Ultra-Violet/Visible (UV/VI) spectrophotometry which determines the transmission of UV/VIS light through a sample. A light wavelength of 600 nm has been shown to be adequate for characterizing the degree of light transmittance through a sample. Typically, it is best to follow the specific instructions relating to the specific spectrophotometer being used. In general, the procedure for measuring percent transmittance starts by setting the spectrophotometer to 600 nm. Then a calibration "blank" is run to calibrate the readout to 100 percent transmittance. A single test sample is then placed in a cuvette designed to fit the specific spectrophotometer and care is taken to insure no air bubbles are within the sample before the % T is measured by the spectrophotometer at 600 nm. Alternatively, multiple samples can be measured simultaneously by using a spectrophotometer such as the SpectraMax M-5 available from Molecular Devices. Multiple dilution samples can be prepared within a 96 well plate (VWR catalog #82006-448) and then transferred to a 96 well visible flat bottom plate (Greiner part #655-001), ensuring that no air bubbles are within the sample. The flat bottom plate is placed within the SpectraMax M-5 and % T measured using the Software Pro v.5™ software available from Molecular Devices.

B. Lasentec FBRM Method

The composition does not contain coacervate prior to dilution. One option to measure lack of coacervate is using Lasentec FBRM Method with no dilution. A Lasentec Focused Beam Reflectance Method (FBRM) [model S400A available from Mettler Toledo Corp] may be used to determine floc size and amount as measured by chord length and particle counts/sec (counts per sec). The composition containing only surfactants substantially free from sulfates, optionally amphoteric surfactants, cationic deposition polymers and a low level of inorganic salt does not contain flocs. The composition with other materials added does not contain flocs of different particle size than the particle size of the other materials added.

C. Coacervate Quantity

Coacervate Centrifuge Method

Presence of coacervate can be measured by centrifuging a cleansing composition and measuring coacervate gravimetrically. The cleansing composition containing only surfactants substantially free from sulfates, amphoteric surfactants, cationic deposition polymers and a low level of inorganic salt is centrifuged for 20 minutes at 9200 rpm using a Beckman Couller TJ25 centrifuge. Several time/rpm combinations can be used. The supernatant is then removed and the remaining settled coacervate assessed gravimetrically. % Coacervate is calculated as the weight of settled coacervate as a percentage of the weight of cleansing composition added to the centrifuge tube using the equation below. This quantifies the percentage of the cleansing composition the participates in the coacervate phase. The % coacervate for composition containing surfactants substantially free from sulfates, optionally amphoteric surfactants, cationic deposition polymers and a low level of inorganic salt is 0%.

$$\%\ \text{Coacervate} = \frac{\text{Weight of settled coacervate}}{\text{Weight of shampoo added to centrifuge tube}} \times 100$$

D. Lather Characterization

Kruss DFA100 Lather Characterization

A cleansing composition dilution of 10 parts by weight water to 1 part by weight cleanser is prepared. The shampoo dilution is dispensed into the Kruss DFA100 which generates the lather and measures lather properties.

E. Wet Combing Characterization

Wet Combing Force Method

Hair switches of 4 grams general population hair at 8 inches length are used for the measurement. Each hair switch is treated with 4 cycles (1 lather/rinse steps per cycle, 0.1 gm cleansing composition/gm hair on each lather/rinse step, drying between each cycle) with the cleansing composition. Four switches are treated with each shampoo. The hair is not dried after the last treatment cycle. While the hair is wet, the hair is pulled through the fine tooth half of two Beautician 3000 combs. Force to pull the hair switch through the combs is measured by a friction analyzer (such as Instron or MTS tensile measurement) with a load cell and outputted in gram-force (gf). The pull is repeated for a total of five pulls per switch. Average wet combing force is calculated by averaging the force measurement from the five pulls across the four hair switches treated with each cleansing composition. Data can be shown as average wet combing force through one or both of the two combs.

EXAMPLES

The following Examples illustrate various cleansing compositions. Each cleansing composition is prepared by conventional formulation and mixing techniques.

TABLE 1

| Experiments with combination of surfactants and cationic polymers (Active %) | | | | | | | | |
|---|---|---|---|---|---|---|---|---|
| | Inventive Examples | | | | | | | |
| | 1 | 2 | 3 | 4 | 5 | 6 | 7 | 8 |
| Disodium laureth sulfosuccinate [1] | 10.0 | 10.0 | 10.0 | — | 10.0 | — | 10.0 | 10.0 |
| Sodium Lauroyl methyl isethionate[2] | — | — | — | 10.0 | — | — | — | — |
| Sodium cocoyl isethionate [3] | 5.0 | 5.0 | 5.0 | 5.0 | 5.0 | 5.0 | 5.0 | 5.0 |
| Lauramidopropyl betaine [4] | 5.0 | 5.0 | 10.0 | 5.8 | 10.0 | 3.0 | 10.0 | 10.0 |
| Cocamidopropyl betaine [5] | — | — | — | — | — | — | — | — |
| Sodium cocoyl alaninate [6] | 5.0 | — | — | — | — | — | — | — |
| Sodium cocoyl glutamate [7] | — | 5.0 | — | 5.0 | — | 15.0 | — | — |
| Sodium cocoyl alaninate [8] | — | — | — | — | — | — | — | — |
| Disodium cocoyl glutamate [9] | — | — | — | — | — | — | — | — |
| Polyquaternium10[10] | 0.35 | 0.35 | 0.35 | 0.35 | 0.35 | 0.20 | 0.35 | 0.35 |
| Polyquaternium 6[11] | 0.20 | 0.20 | 0.20 | 0.20 | 0.20 | — | 0.20 | 0.20 |
| NaCl[12] | — | — | — | — | 0.68 | — | — | — |
| Tetrasodium ethylenediaminetetra acetate [13] | 0.16 | 0.16 | 0.16 | 0.16 | 0.16 | 0.16 | 0.16 | 0.16 |
| Sodium benzoate[14] | 0.24 | 0.24 | 0.24 | 0.24 | 0.24 | 0.24 | 0.24 | 0.50 |
| Methyl chloro isothiazolinone and Methyl isothiazolinone [15] | 0.0004 | 0.0004 | 0.0004 | 0.0004 | 0.0004 | 0.0004 | 0.0004 | — |
| Dimethiconol and Dimethicone[26] | — | — | — | — | — | — | 2.0 | — |
| Trihydroxystearin[24] | — | — | — | — | — | — | 0.1 | — |
| Dimethiconol[25] | — | — | — | — | — | — | — | 2.0 |
| Perfume | 2.0 | 2.0 | 2.0 | 2.0 | 2.0 | 2.0 | 2.0 | 2.0 |
| Citric acid[16] | To pH 6.0 | To pH 6.0 | To pH 6.0 | To pH 6.0 | To pH 6.0 | To pH 6.0 | To pH 6.0 | To pH 2.0 |
| DI Water | Q.S. | Q.S. | Q.S. | Q.S. | Q.S. | Q.S. | Q.S. | Q.S. |
| Viscosity, cps | 179 | 474 | 1958 | 1275 | 1641 | 43 | 8500 | 1800 |
| Total NaCl % | 0.08 | 0.14 | 0.12 | 0.14 | 0.80 | 0.24 | 0.12 | 0.12 |
| coacervate present | No | No | No | No | No | No | No | No |
| Coacervate phase after 1:9 dilution | Yes | Yes | Yes | Yes | Yes | Yes | Yes | Yes |

TABLE 2

| Comparative examples (Active %) | | | | | |
|---|---|---|---|---|---|
| | Comparative Examples | | | | |
| | A | B | C | D | E |
| Disodium laureth sulfosuccinate [1] | 10.0 | 10.0 | — | 10.0 | — |
| Sodium Lauroyl methyl isethionate[2] | — | — | 10.0 | — | — |
| Sodium cocoyl isethionate [3] | 5.0 | 5.0 | 5.0 | 5.0 | 5 |
| Lauramidopropyl betaine [4] | 5.0 | 10.0 | 5.8 | — | 3 |
| Cocamidopropyl betaine [5] | — | — | — | 10.0 | — |
| Sodium cocoyl alaninate [6] | — | — | — | — | — |
| Sodium cocoyl glutamate [7] | — | — | — | — | — |

TABLE 2-continued

| Comparative examples (Active %) | | | | | |
|---|---|---|---|---|---|
| | Comparative Examples | | | | |
| | A | B | C | D | E |
| Sodium cocoyl alaninate [8] | 5.0 | — | — | — | — |
| Disodium cocoyl glutamate [9] | — | — | 5.0 | — | 15 |
| Polyquaternium10[10] | 0.35 | 0.35 | 0.35 | 0.35 | 0.20 |
| Polyquaternium 6[11] | 0.20 | 0.20 | 0.20 | 0.20 | — |
| NaCl[12] | — | 0.96 | — | — | — |
| Tetrasodiumethylenediaminetetraacetate [13] | 0.16 | 0.16 | 0.16 | 0.16 | 0.16 |
| Sodium benzoate[14] | 0.24 | 0.24 | 0.24 | 0.24 | 0.24 |
| Methyl chloro isothiazolinone and Methyl isothiazolinone [15] | 0.0004 | 0.0004 | 0.0004 | 0.0004 | 0.0004 |
| Perfume | 2.0 | 2.0 | 2.0 | 2.0 | 2.0 |
| Citric acid[16] | To pH 6.0 | To pH 6.0 | To pH 6.0 | To pH 6.0 | To pH 6.0 |
| DI Water | Q.S. | Q.S. | Q.S. | Q.S. | Q.S. |
| Viscosity, cps | 2096 | 1555 | 3634 | 157 | 43 |
| Total NaCl % | 1.1 | 1.1 | 1.2 | 1.7 | 2.75 |
| Coacervate present | Yes | Yes | Yes | Yes | Yes |

TABLE 3

| Experiments with single surfactant and polymer (all materials in table are active). | | | | | |
|---|---|---|---|---|---|
| | Inventive Examples | | | | |
| EXAMPLE# | 9 | 10 | 11 | 12 | 13 |
| Water | 74.87% | 74.57% | 83.48% | 83.50% | 74.17% |
| GUAR HYDROXYPROPYLTRIMONIUM CHLORIDE [18] | 0.30% | 0.30% | 0.30% | 0.30% | 0.30% |
| DISODIUM LAURETH SULFOSUCCINATE[1] | 23.18% | 23.18% | — | — | 23.18% |
| Sodium Cocoyl Alaninate[6] | — | — | 14.22% | — | — |
| Sodium cocoyl Glycinate[17] | | | — | 14.24% | |
| Citric Acid[16] | 0.20% | 0.20% | 0.20% | 0.10% | 0.20% |
| Sodium Benzoate [14] | 0.25% | 0.25% | 0.25% | 0.25% | 0.25% |
| Cocamidopropyl Betaine[5] | 0.00% | 0.00% | 0.00% | 0.00% | 0.00% |
| Perfume | 0.90% | 0.90% | 0.90% | 0.90% | 0.90% |
| Methylchloroisothiazolinone/ Methylisothiazolinone[15] | 0.00075% | 0.00075% | 0.00075% | 0.00075% | 0.00075% |
| Total Sodium Chloride (including from surfactant) | 0.30% | 0.60% | 0.65% | 0.71% | 1.0% |
| Coacervate present | No | No | No | No | No |

| | Comparative examples | | | |
|---|---|---|---|---|
| EXAMPLE# | F | G | H | I |
| Water | 73.39% | 73.32% | 80.91% | 81.00% |
| GUAR HYDROXYPROPYLTRIMONIUM CHLORIDE [18] | 0.30% | 0.30% | 0.30% | 0.30% |
| DISODIUM LAURETH SULFOSUCCINATE[1] | 22.21% | 23.18% | 0.00% | — |
| Sodium Cocoyl Alaninate[6] | — | — | 14.22% | — |
| Sodium cocoyl Glycinate[17] | | | | 14.24% |
| Citric Acid[16] | 0.20% | 0.20% | 0.20% | 0.10% |
| Sodium Benzoate [14] | 0.25% | 0.25% | 0.25% | 0.25% |
| Cocamidopropyl Betaine[5] | 1.50% | 0.00% | 0.00% | 0.00% |
| Perfume | 0.90% | 0.90% | 0.90% | 0.90% |
| Methylchloroisothiazolinone/ Methylisothiazolinone[15] | 0.00075% | 0.00075% | 0.00075% | 0.00075% |
| Total Sodium Chloride (including from surfactant) | 1.25% | 1.75% | 3.12% | 3.21% |
| Coacervate present | Yes | Yes | Yes | Yes |

TABLE 4

| Inventive Examples (Active %) | | | | | |
|---|---|---|---|---|---|
| | Inventive Examples | | | | |
| | 14 | 15 | 16 | 17 | 18 |
| Lauramidopropyl Betaine[4] | 9.75 | 9.75 | 9.75 | 9.75 | 9.75 |
| Sodium Cocoyl Isethionate[3] | 6 | 6 | 6 | 6 | 6 |
| Sodium Lauroyl Sarcosinate[19] | — | — | — | 4 | — |
| Polyquaternium-10[20] | — | — | 0.8 | 0.8 | 0.8 |
| Polyquaternium-10[10] | | 0.8 | — | — | — |
| Guar Hydroxypropyltrimonium Chloride[21] | 0.8 | — | — | — | — |
| Acrylates Copolymer[23] | — | — | — | — | 0.06 |
| Water-USP Purified, Preservatives, pH Adjusters, Fragrance and Optional Components | Q.S. to 100 | Q.S. to 100 | Q.S. to 100 | Q.S. to 100 | Q.S. to 100 |
| Total Sodium Chloride (including from surfactant) | 0.1 | 0.1 | 0.1 | 0.1 | 0.1 |
| Coacervate present before dilution | No | No | No | No | No |

TABLE 5

| Sodium Chloride leveling experiments (Active %) | | | |
|---|---|---|---|
| | Inventive Example 19 | Inventive Example 20 | Comparative Example J |
| Cocamidopropyl Betaine[22] | 7.12 | 7.12 | 7.12 |
| Sodium Cocoyl Isethionate[3] | 6 | 6 | 6 |
| Polyquaternium-10[20] | 0.8 | 0.8 | 0.8 |
| Sodium Chloride[12] | 0.17 | 0.67 | 1.17 |
| Water-USP Purified, Preservatives, pH Adjusters, Fragrance and Optional Components | Q.S. to 100 | Q.S. to 100 | Q.S. to 100 |
| Total Sodium Chloride (including from surfactant) | 0.22 | 0.72 | 1.22 |
| Coacervate present | No | No | Yes |

1. Chemccinate™ DSLS from Lubrizol
2. Iselux® from Innospec
3. Jordapon® CI Prill from BASF
4. Mackam DAB ULS from Solvay
5. Amphosol® HCA-HP from Stepan
6. Eversoft ACS (low salt) from Sino Lion
7. Sodium cocoyl glutamate, Hostapon CGN (low salt) from Clariant
8. Eversoft ACS-30S (regular salt level) from Sino Lion
9. Eversoft™ UCS-50SG from Sino-Lion
10. Poly JR-30M from Amerchol
11. Mirapol® 100s from Solvay
12. Sodium chloride from Norton International Inc.
13. Versene™ 220 from Dow®
14. Sodium benzoate from Kalama Chemical
15. Kathon™ CG from Dow®
16. Citric acid from ADM
17. Amilite GCS-12 from Ajinomoto
18. Jaguar C500 from Solvay
19. Crodasinic LS30/NP from Croda
20. UCARE™ Polymer LR-30M from DOW
21. Dehyquart Guar from BASF
22. Dehyton PK 45 from BASF with Sodium Chloride removed, resulting in 33.05% Dry Residue, 0.21% Sodium Chloride
23. Rheocare TTA from BASF
24. Thixcin R from Elementis
25. Xiameter MEM-1872 Emulsion from DOW
26. Belsil DM 5500 E from Wacker It will be appreciated that other modifications of the present disclosure are within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified. A level of perfume and/or preservatives may also be included in the following examples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleansing composition comprising:

a) about 3 wt % to about 35 wt % of an acyl taurate anionic surfactant;

b) about 3 wt % to about 15% of an amphoteric surfactant;

c) about 0.01 wt % to about 2 wt % of a cationic polymer having a weight average molecular weight of 300,000 g/mol to about 3,000,000 g/mol;

d) 0 wt % to about 1.0 wt % of inorganic salts; and e) an aqueous carrier, wherein the composition is substantially free of sulfate-based surfactant and does not form a coacervate prior to use.

2. The composition of claim 1, wherein the acyl taurate anionic surfactant is selected from sodium, ammonium and potassium salts of methyl cocoyl taurate, methyl lauroyl taurate and methyl oleoyl taurate, and combinations thereof.

3. The composition of claim 2, wherein the acyl taurate anionic surfactant is selected from sodium methyl cocoyl taurate, sodium methyl lauroyl taurate, sodium methyl oleoyl taurate and combinations thereof.

4. The composition of claim 1, wherein the cationic polymer is selected from the group consisting of cationic guars, cationic cellulose, cationic synthetic homopolymers, cationic synthetic copolymers, and combinations thereof.

5. The composition of claim 4, wherein the cationic polymer is selected from the group consisting of hydroxypropyltrimonium guar, Polyquaternium 10, Polyquaternium 6, and combinations thereof.

6. The composition of claim 1 wherein the inorganic salt is selected from the group consisting of sodium chloride, potassium chloride, sodium sulfate, ammonium chloride, sodium bromide, and combinations thereof.

7. The composition of claim 1, wherein the composition has a viscosity lower than about 5000 cps.

8. The composition of claim 1 wherein the composition is delivered as a foam.

9. The composition of claim 8, wherein the composition comprises a propellant.

10. The composition of claim 8, wherein the foam is delivered from a mechanical pump foamer.

11. The composition of claim 1 further comprising silicone conditioning agents.

12. The composition of claim 11, wherein the silicone conditioning agent is an emulsion with particle size of less than about 30 microns.

13. The composition of claim 1, wherein the amphoteric surfactant is selected from the group consisting of betaines, sultaines, hydroxysultanes, amphohydroxypropyl sulfonates, alkyl amphoactates, alkyl amphodiacetates and combination thereof.

* * * * *